US012633409B2

(12) United States Patent
Christie

(10) Patent No.: US 12,633,409 B2
(45) Date of Patent: **\*May 19, 2026**

(54) WIRELESS LOCATION LEARNING

(71) Applicant: Hill-Rom Services, Inc., Batesville, IN (US)

(72) Inventor: John D. Christie, Batesville, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/789,785

(22) Filed: Jul. 31, 2024

(65) Prior Publication Data

US 2024/0395401 A1 Nov. 28, 2024

Related U.S. Application Data

(63) Continuation of application No. 17/308,122, filed on May 5, 2021, now Pat. No. 12,080,420.

(Continued)

(51) Int. Cl.
*G16H 40/67* (2018.01)
*G16H 40/20* (2018.01)
*H04W 88/08* (2009.01)

(52) U.S. Cl.
CPC ............. *G16H 40/67* (2018.01); *G16H 40/20* (2018.01); *H04W 88/08* (2013.01)

(58) Field of Classification Search
CPC ...... G16H 40/67; G16H 40/20; H04B 17/318; H04W 88/08; H04W 4/33; H04W 4/029;

(Continued)

(56) References Cited

U.S. PATENT DOCUMENTS

| 7,319,386 B2 | 1/2008 | Collins, Jr. et al. |
| 7,538,659 B2 | 5/2009 | Ulrich et al. |
| (Continued) |

FOREIGN PATENT DOCUMENTS

| CN | 106921942 A | 7/2014 |
| CN | 107920332 A | 4/2018 |
| (Continued) |

OTHER PUBLICATIONS

Gholamhosseini et al., Hospital Real-Time Location System (A Practical Approach in Healthcare): a Narrative Review Article. Iran J Public Health. Apr. 2019;48(4):593-602. PMID: 31110969; PMCID: PMC6500521 (Year: 2019).*

(Continued)

*Primary Examiner* — Joy Chng
(74) *Attorney, Agent, or Firm* — Barnes & Thornburg LLP

(57) ABSTRACT

A wireless locating system and method include receiving first messages at a server. The first messages include bed location data entered manually on a user interface of a first patient bed. The first messages also include signal strength data from a plurality of wireless access points in communication with the first patient bed. A first signal strength profile for the first patient bed at a first location is built by the server. The first patient bed is removed from the first location and a second bed is moved into the first location. The second patient bed does not have manual location data entry capability. A second signal strength profile is built by the server for the second patient bed. The server compares the second signal strength profile with the first signal strength profile and determines that the second patient bed is at the first location if the second signal strength profile matches the first signal strength profile.

19 Claims, 9 Drawing Sheets

Related U.S. Application Data

(60) Provisional application No. 63/031,688, filed on May 29, 2020.

(58) Field of Classification Search
CPC ............. G01S 2205/10; G01S 5/02524; G01S 5/02527
USPC ......................................................... 705/2–3
See application file for complete search history.

(56) References Cited

U.S. PATENT DOCUMENTS

| | | | |
|---|---|---|---|
| 8,046,625 | B2 | 10/2011 | Ferguson et al. |
| 8,164,444 | B2 | 4/2012 | Anderson et al. |
| 8,169,304 | B2 | 5/2012 | Schuman, Sr. et al. |
| 8,384,526 | B2 | 2/2013 | Schuman, Sr. et al. |
| 8,598,995 | B2 | 12/2013 | Schuman et al. |
| 9,838,836 | B2 | 12/2017 | Hayes et al. |
| 9,937,090 | B2 | 4/2018 | Hayes et al. |
| 10,097,956 | B2 | 10/2018 | Cho et al. |
| 10,257,063 | B2 | 4/2019 | Bhimavarapu et al. |
| 12,080,420 | B2 | 9/2024 | Christie |
| 2007/0210917 | A1 | 9/2007 | Collins, Jr. et al. |
| 2009/0212925 | A1 | 8/2009 | Schuman, Sr. et al. |
| 2009/0212926 | A1 | 8/2009 | Du et al. |
| 2009/0217080 | A1 | 8/2009 | Ferguson et al. |
| 2015/0081335 | A1* | 3/2015 | Dixon .................... H04W 4/33 705/2 |
| 2015/0082542 | A1* | 3/2015 | Hayes .................... H04W 4/02 455/456.1 |
| 2016/0094947 | A1 | 3/2016 | Shen et al. |
| 2016/0345286 | A1* | 11/2016 | Jamieson ............... H04B 17/12 |
| 2017/0323555 | A1 | 11/2017 | Embree et al. |
| 2018/0161225 | A1 | 6/2018 | Zerhusen et al. |
| 2020/0268579 | A1 | 8/2020 | Heimbrock et al. |
| 2020/0345568 | A1 | 11/2020 | Heimbrock et al. |
| 2020/0364662 | A1* | 11/2020 | Avery, Jr. .......... G06Q 10/0875 |
| 2021/0375449 | A1 | 12/2021 | Christie |

FOREIGN PATENT DOCUMENTS

| | | | | |
|---|---|---|---|---|
| EP | 2860651 | A1 | 4/2015 | |
| EP | 2622918 | B1 * | 10/2015 | ......... G01S 5/02521 |
| EP | 2845162 | B1 | 12/2019 | |
| WO | 2019112844 | A | 6/2019 | |

OTHER PUBLICATIONS

Gholamhosseini et al., Hospital Real-Time Location System (A Practical Approach in Healthcare): a Narrative Review Article. Iran J Public Health, Apr. 2019; 48(4): 593-602. PMID: 31110969; PMCID: PMC6500521 (Year: 2019) (9 pages).

European Search Report for European Patent Application No. 21175535.0 dated Oct. 22, 2021 (8 pages).

* cited by examiner

144

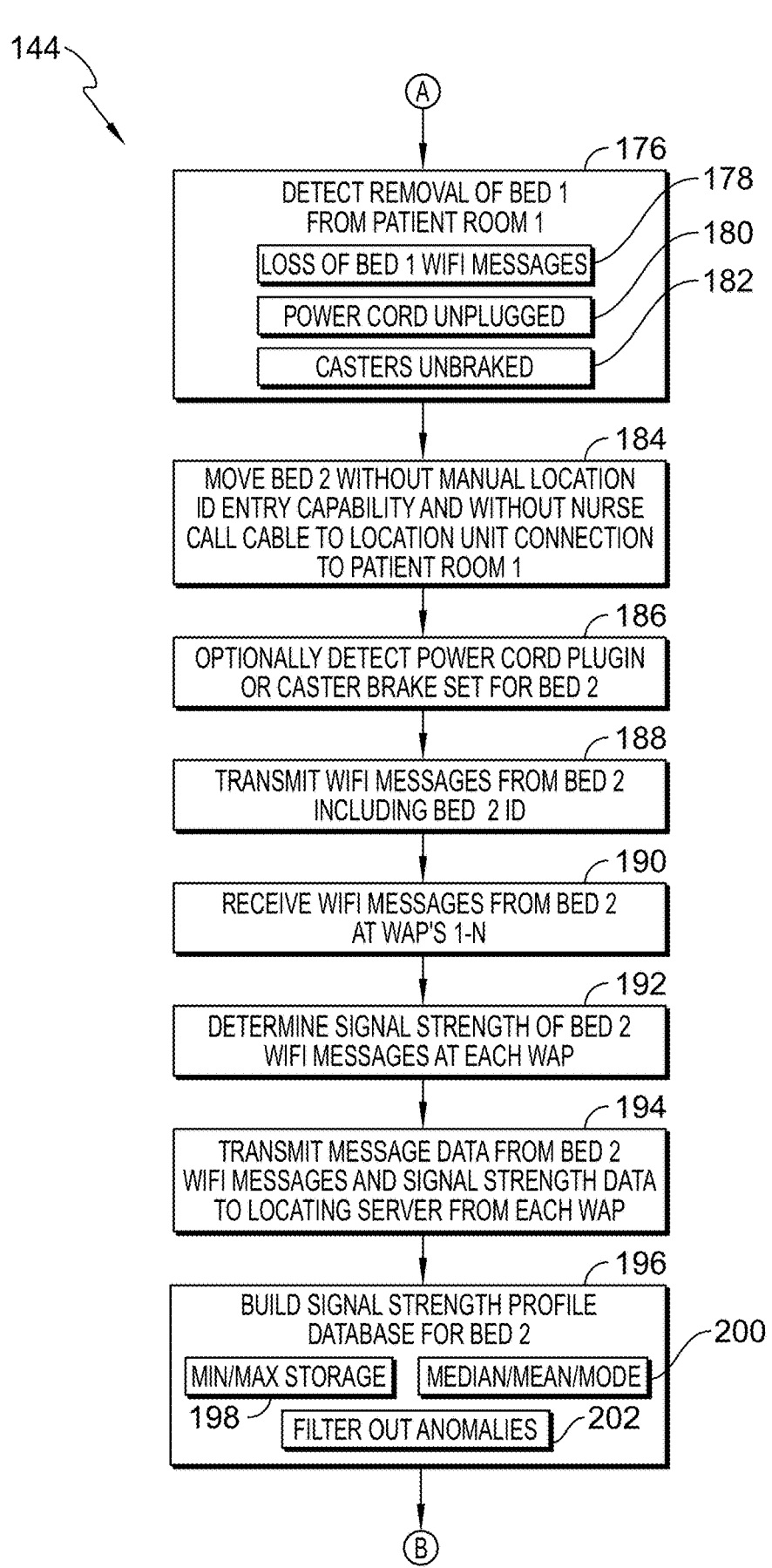

Ⓐ

DETECT REMOVAL OF BED 1
FROM PATIENT ROOM 1 ⌐176
┌──────────────────────────────┐
│ LOSS OF BED 1 WIFI MESSAGES  │ ⌐178
├──────────────────────────────┤
│ POWER CORD UNPLUGGED          │ ⌐180
├──────────────────────────────┤
│ CASTERS UNBRAKED              │ ⌐182
└──────────────────────────────┘

MOVE BED 2 WITHOUT MANUAL LOCATION
ID ENTRY CAPABILITY AND WITHOUT NURSE
CALL CABLE TO LOCATION UNIT CONNECTION
TO PATIENT ROOM 1 ⌐184

OPTIONALLY DETECT POWER CORD PLUGIN
OR CASTER BRAKE SET FOR BED 2 ⌐186

TRANSMIT WIFI MESSAGES FROM BED 2
INCLUDING BED 2 ID ⌐188

RECEIVE WIFI MESSAGES FROM BED 2
AT WAP'S 1-N ⌐190

DETERMINE SIGNAL STRENGTH OF BED 2
WIFI MESSAGES AT EACH WAP ⌐192

TRANSMIT MESSAGE DATA FROM BED 2
WIFI MESSAGES AND SIGNAL STRENGTH DATA
TO LOCATING SERVER FROM EACH WAP ⌐194

BUILD SIGNAL STRENGTH PROFILE
DATABASE FOR BED 2 ⌐196
┌──────────────────┐   ┌──────────────────────┐
│ MIN/MAX STORAGE  │   │ MEDIAN/MEAN/MODE      │ ⌐200
└──────────────────┘   └──────────────────────┘
     198
         ┌──────────────────────┐
         │ FILTER OUT ANOMALIES  │ ⌐202
         └──────────────────────┘

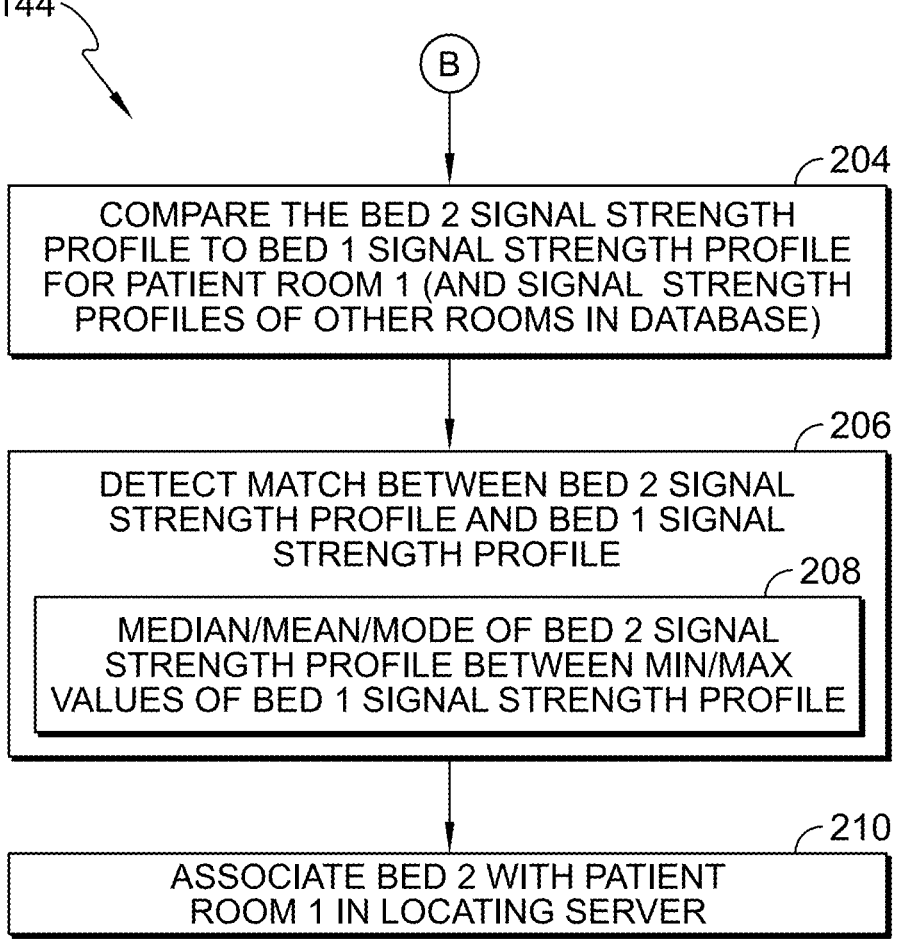

144

B

204

COMPARE THE BED 2 SIGNAL STRENGTH
PROFILE TO BED 1 SIGNAL STRENGTH PROFILE
FOR PATIENT ROOM 1 (AND SIGNAL STRENGTH
PROFILES OF OTHER ROOMS IN DATABASE)

206

DETECT MATCH BETWEEN BED 2 SIGNAL
STRENGTH PROFILE AND BED 1 SIGNAL
STRENGTH PROFILE

208

MEDIAN/MEAN/MODE OF BED 2 SIGNAL
STRENGTH PROFILE BETWEEN MIN/MAX
VALUES OF BED 1 SIGNAL STRENGTH PROFILE

210

ASSOCIATE BED 2 WITH PATIENT
ROOM 1 IN LOCATING SERVER

| BED 1 SIGNAL STRENGTH PROFILE FOR ROOM 1 | | | | | |
|---|---|---|---|---|---|
| WAP # | MIN | MAX | MEAN | MEDIAN | MODE |
| WAP 1 (FREQUENCY 1) | $SS_{MIN\ 1\text{-}1}$ | $SS_{MAX\ 1\text{-}1}$ | MEAN 1-1 | MEDIAN 1-1 | MODE 1-1 |
| WAP 2 (FREQUENCY 2) | $SS_{MIN\ 2\text{-}1}$ | $SS_{MAX\ 2\text{-}1}$ | MEAN 2-1 | MEDIAN 2-1 | MODE 2-1 |
| WAP 3 (FREQUENCY 3) | $SS_{MIN\ 3\text{-}1}$ | $SS_{MAX\ 3\text{-}1}$ | MEAN 3-1 | MEDIAN 3-1 | MODE 3-1 |
| $\vdots$ | $\vdots$ | $\vdots$ | $\vdots$ | $\vdots$ | $\vdots$ |
| WAP N (FREQUENCY N) | $SS_{MIN\ N\text{-}1}$ | $SS_{MAX\ N\text{-}1}$ | MEAN N-1 | MEDIAN N-1 | MODE N-1 |

| BED 2 SIGNAL STRENGTH PROFILE | | | | | |
|---|---|---|---|---|---|
| WAP # | MIN | MAX | MEAN | MEDIAN | MODE |
| WAP 1 (FREQUENCY 1) | $SS_{MIN\ 1\text{-}2}$ | $SS_{MAX\ 1\text{-}2}$ | MEAN 1-2 | MEDIAN 1-2 | MODE 1-2 |
| WAP 2 (FREQUENCY 2) | $SS_{MIN\ 2\text{-}2}$ | $SS_{MAX\ 2\text{-}2}$ | MEAN 2-2 | MEDIAN 2-2 | MODE 2-2 |
| WAP 3 (FREQUENCY 3) | $SS_{MIN\ 3\text{-}2}$ | $SS_{MAX\ 3\text{-}2}$ | MEAN 3-2 | MEDIAN 3-2 | MODE 3-2 |
| $\vdots$ | $\vdots$ | $\vdots$ | $\vdots$ | $\vdots$ | $\vdots$ |
| WAP N (FREQUENCY N) | $SS_{MIN\ N\text{-}2}$ | $SS_{MAX\ N\text{-}2}$ | MEAN N-2 | MEDIAN N-2 | MODE N-2 |

*FIG. 5*

WIRELESS LOCATION LEARNING

The present application is a continuation of U.S. application Ser. No. 17/308,122, filed May 5, 2021, now U.S. Pat. No. 12,080,420, which claims priority, under 35 U.S.C. § 119(e), to U.S. Provisional Application No. 63/031,688, filed May 29, 2020, each of which is hereby incorporated by reference herein in its entirety.

BACKGROUND

The present disclosure relates to systems and methods of tracking the locations of equipment within a building and particularly, to systems and methods of tracking the locations of patient care equipment in a healthcare facility. More particularly, the present disclosure relates to wireless locating systems and methods of tracking the locations of equipment in a building.

It is desirable to know the locations of some equipment within a building. For example, it is desirable to know the locations of patient care equipment, such as patient beds, within a healthcare facility. Known location systems include, for example, locating tags that are attached to equipment (and people) and that communicate tag identification data ("tag ID's") wirelessly with receivers or transceivers of location units mounted at fixed locations throughout a healthcare facility. The location units, in turn, transmit the tag ID's and location unit ID's to a remote server which then correlates the tag ID's and the associated equipment (or persons) to the particular locations corresponding to the location unit ID's. In such systems, the wireless communication employed is oftentimes infrared (IR) although ultrasound communications are also known.

Radio frequency (RF) communication is not used as often in locating systems because RF signals pass through walls, floors, and ceilings and therefore, can be received by multiple location units which results in ambiguity as to where a particular locating tag is actually located. However, there are known locating systems in which a location unit communicates a location ID to a locating tag by an infrared transmission and then the locating tag communicates the tag ID and the location ID via an RF signal to an RF receiver or transceiver such as a wireless fidelity (WiFi) access point (WAP). However, in each of the foregoing types of known wireless locating systems, dedicated locating system infrastructure, such as the location units, are required even when the locating system ultimately interfaces with the WiFi network of the facility.

In the case of patient beds, wired connections such as via 37-pin nurse call cables, to bed interface units mounted at fixed locations, such as patient rooms, are also known. The bed interface units are, in turn, connected to other nurse call infrastructure via cabling and sometimes other hardware, such as gateways, network switches, and the like. The bed interface unit ID's correlate to the locations of the patient beds and so communication between a nurse call server, for example, and a locating server allows for the locations of the patient beds to be known, but again, such an arrangement involves the installation of a large amount of infrastructure that is not otherwise needed in the computer network of the healthcare facility. Accordingly, there is a need for a wireless locating system in a healthcare facility, in particular, for determining the locations of patient care equipment, such as hospital beds, but without the need for the installation of infrastructure beyond that of the pre-existing computer network of the healthcare facility.

SUMMARY

An apparatus, system, or method may comprise one or more of the features recited in the appended claims and/or the following features which, alone or in any combination, may comprise patentable subject matter:

According to a first aspect of the present disclosure, a wireless locating method may include receiving first messages at a server. The first messages may include bed location data that may be entered manually on a user interface of a first patient bed. The first messages may include signal strength data from a plurality of wireless access points that may be in communication with the first patient bed. The method of the first aspect may further include building with the server a first signal strength profile for a first location that may correspond to the bed location data received from the first patient bed. The first signal strength profile may be based on the signal strength data that may be contained in the first messages. The method of the first aspect may also include receiving second messages at the server. The second messages may be devoid of any bed location data. The second messages may include signal strength data from the wireless access points that may be in communication with a second patient bed. The method of the first aspect may further include building with the server a second signal strength profile that may be based on the signal strength data contained in the second messages, comparing with the server the second signal strength profile with the first signal strength profile, and determining with the server that the second patient bed may be at the first location if the second signal strength profile matches the first signal strength profile.

In some embodiments of the first aspect, the first messages may include power plug status data that may be indicative of whether a power plug of the first patient bed may be plugged into a power receptacle. Optionally, building the first signal strength profile may occur only if the power plug status data indicates that the power plug of the first patient bed may be plugged into the power receptacle. Further optionally, the first messages include caster brake status data indicative of whether one or more casters of the first patient bed is braked or released and building the first signal strength profile may occur only if the caster brake status data indicates that the one or more casters of the first patient bed may be braked.

If desired, the first messages of the first aspect may include caster brake status data that may be indicative of whether one or more casters of the first patient bed may be braked or released. Optionally, building the first signal strength profile may occur only if the caster brake status data indicates that the one or more casters of the first patient bed may be braked. In some embodiments of the wireless locating method of the first aspect, the second messages may include caster brake status data that may be indicative of whether one or more casters of the second patient bed may be braked or released. Optionally, building the second signal strength profile may occur only if the caster brake status data indicates that the one or more casters of the second patient bed may be braked.

It is contemplated by the present disclosure that the second messages of the first aspect may include power plug status data that may be indicative of whether a power plug of the second patient bed may be plugged into a power receptacle. Optionally, building the second signal strength profile may occur only if the power plug status data indicates that the power plug of the second patient bed is plugged into the power receptacle. Alternatively or additionally, the second messages of the first aspect may include caster brake status data that may be indicative of whether one or more casters of the second patient bed is braked or released. In such embodiments, building the second signal strength profile may occur only if the caster brake status data indicates that the one or more casters of the second patient bed may be braked.

In some embodiments of the wireless locating method of the first aspect, building the first signal strength profile may include receiving the first messages over a threshold amount of time and storing in the server minimum signal strength values and maximum signal strength values for each wireless access point of the plurality of wireless access points that may be in communication with the first patient bed during the threshold amount of time. In such embodiments, determining that the second signal strength profile may match the first signal strength profile may include determining that the signal strength data in the second messages for a preset number of wireless access points of the plurality of wireless access points may be between the respective minimum signal strength values and maximum signal strength values for each of the preset number of wireless access points.

If desired, the preset number of wireless access points may be less than all of the wireless access points in communication with the second patient bed. Alternatively or additionally, the preset number of wireless access points of the first aspect may correspond to a set number of wireless access points that may have highest signal strength from among the plurality of wireless access points in communication with the second patient bed. For example, the set number may be at least four.

It is contemplated by the present disclosure that the wireless locating method of the first aspect may further include filtering out anomalous signal strength data from inclusion in the minimum signal strength values and the maximum signal strength values. For example, the anomalous signal strength data may include signal strength data below a predetermined signal strength threshold.

If desired, the wireless locating method of the first aspect may further include initiating from the server a recalibration request to have the bed location data re-entered manually with the user interface of the first patient bed if the signal strength data of the first messages is indicative of one or more obstructions possibly being present at the first location. Alternatively or additionally, the wireless locating method of the first aspect may further include initiating from the server a recalibration request to have the bed location data re-entered manually with the user interface of the first patient bed if the signal strength data of the first messages is indicative that a wireless network including the plurality of wireless access points may have been updated. Optionally, the wireless network of the first aspect may be determined to be updated by the server in response to one or more wireless access points of the plurality of wireless access points being removed from the wireless network. Further optionally, the wireless network may be determined to be updated by the server in response to one or more additional wireless access points being added to the wireless network.

The present disclosure further contemplates a system for carrying out the method of the first aspect and the system may have any of the features set forth in any one or more of the preceding sentences pertaining to the first aspect. As such, the system of the first aspect may include one or more of the following: the server, the first patient bed, the plurality of wireless access points, and the second patient bed. The present disclosure also contemplates a nontransitory computer-readable medium having instructions stored thereon for carrying out the method of any of the features set forth in any one or more of the preceding sentences pertaining to the first aspect.

According to a second aspect of the present disclosure, a wireless locating method may include receiving first messages at a server. The first messages may include equipment location data that may be entered manually on a user interface of a first piece of equipment. The first messages may include signal strength data from a plurality of wireless access points that may be in communication with the first piece of equipment. The method of the second aspect may further include building with the server a first signal strength profile for a first location that may correspond to the equipment location data that may be received from the first piece of equipment. The first signal strength profile may be based on the signal strength data contained in the first messages. The method of second may also include receiving second messages at the server. The second messages may be devoid of any equipment location data and the second messages may include signal strength data from the wireless access points that may be in communication with a second piece of equipment. The method of the second aspect may further include building with the server a second signal strength profile that may be based on the signal strength data contained in the second messages, comparing with the server the second signal strength profile with the first signal strength profile, and determining with the server that the second piece of equipment may be at the first location if the second signal strength profile matches the first signal strength profile.

In some embodiments of the second aspect, the first messages may include power plug status data that may be indicative of whether a power plug of the first piece of equipment may be plugged into a power receptacle. Optionally, building the first signal strength profile of the second aspect may occur only if the power plug status data indicates that the power plug of the first piece of equipment may be plugged into the power receptacle. If desired, the second messages of the second aspect may include power plug status data that may be indicative of whether a power plug of the second piece of equipment is plugged into a power receptacle. Optionally, building the second signal strength profile may occur only if the power plug status data may indicate that the power plug of the second piece of equipment may be plugged into the power receptacle.

It is contemplated by the present disclosure that building the first signal strength profile of the second aspect may include receiving the first messages over a threshold amount of time and storing in the server minimum signal strength values and maximum signal strength values for each wireless access point of the plurality of wireless access points that may be in communication with the first piece of equipment.

In some embodiments of the wireless locating method of the second aspect, determining that the second signal strength profile may match the first signal strength profile may include determining that the signal strength data in the second messages for a preset number of wireless access points of the plurality of wireless access points may be between the respective minimum signal strength values and maximum signal strength values for each of the preset number of wireless access points. Optionally, the preset number of wireless access points may be less than all of the wireless access points that may be in communication with the second piece of equipment. If desired, the preset number of wireless access points may correspond to a set number of wireless access points that may have highest signal strength from among the plurality of wireless access points that may be in communication with the second piece of equipment. For example, the set number may be at least four.

It is contemplated by the present disclosure that the wireless locating method of the second aspect may further include filtering out anomalous signal strength data from inclusion in the minimum signal strength values and the maximum signal strength values. For example, the anomalous signal strength data may include signal strength data below a predetermined signal strength threshold.

If desired, the wireless locating method of the second aspect may further include initiating from the server a recalibration request to have the equipment location data re-entered manually with the user interface of the first piece of equipment if the signal strength data of the first messages may be indicative of one or more obstructions possibly being present at the first location. Alternatively or additionally, the wireless locating method of the second aspect may further include initiating from the server a recalibration request to have the equipment location data re-entered manually with the user interface of the first piece of equipment if the signal strength data of the first messages is indicative that a wireless network including the plurality of wireless access points may have been updated. Optionally, the wireless network of the second aspect may be determined to be updated by the server in response to one or more wireless access points of the plurality of wireless access points being removed from the wireless network. Further optionally, the wireless network of the second aspect may determined to be updated by the server in response to one or more additional wireless access points being added to the wireless network.

The present disclosure further contemplates a system for carrying out the method of the second aspect and the system may have any of the features set forth in any one or more of the preceding sentences pertaining to the second aspect. As such, the system of the second aspect may include one or more of the following: the server, the first piece of equipment, the plurality of wireless access points, and the second piece of equipment. The present disclosure also contemplates a nontransitory computer-readable medium having instructions stored thereon for carrying out the method of any of the features set forth in any one or more of the preceding sentences pertaining to the second aspect.

According to a third aspect of the present disclosure, a wireless locating method may include entering a location identification (ID) on a graphical user interface (GUI) of a first patient bed that may have manual location ID entry capability. The location ID may correlate to a patient room in which the first patient bed may be located. The method of the third aspect may also include transmitting first patient bed wireless fidelity (WiFi) messages from the first patient bed that may include the location ID and a first bed ID for receipt by a plurality of wireless access points (WAP's) of a computer network of a healthcare facility. The method of the third aspect may further include determining signal strengths of the first patient bed WiFi messages that may be received at each of the WAP's of the plurality of WAP's. Furthermore, the method of the third aspect may include storing the signal strengths of the first patient bed WiFi messages as a first patient bed signal strength profile in memory of a locating server. The first patient bed signal strength profile may be indicative of the patient room in which the first patient bed may be located. The method of the third aspect may further include removing the first patient bed from the patient room and transporting a second patient bed to the patient room. The second patient bed may lack manual location ID entry capability. Additionally, the method of the third aspect may also include transmitting second patient bed WiFi messages from the second patient bed that may include a second bed ID for receipt by the plurality of WAP's of the computer network of the healthcare facility. The method of the third aspect still further may include determining signal strengths of the second patient bed WiFi messages that may be received at each of the WAP's of the plurality of WAP's, storing the signal strengths of the second patient bed WiFi messages as a second patient bed signal strength profile in memory of the locating server, and comparing the second patient bed signal strength profile with the first bed signal strength profile. If the second patient bed signal strength profile of the third aspect substantially matches the first patient bed signal strength profile of the third aspect, the method of the third aspect may also include determining by the locating server that the second patient bed may be located in the patient room.

In some embodiments of the third aspect, the first WiFi messages may include power plug status data that may be indicative of whether a power plug of the first patient bed may be plugged into a power receptacle. Optionally, building the first signal strength profile of the third aspect may occur only if the power plug status data indicates that the power plug of the first patient bed may be plugged into the power receptacle. Further optionally, the first WiFi messages of the third aspect may include caster brake status data that may be indicative of whether one or more casters of the first patient bed may be braked or released and building the first signal strength profile may occur only if the caster brake status data indicates that the one or more casters of the first patient bed may be braked.

If desired, the first WiFi messages of the third aspect may include caster brake status data that may be indicative of whether one or more casters of the first patient bed may be braked or released and building the first signal strength profile may occur only if the caster brake status data indicates that the one or more casters of the first patient bed may be braked. Alternatively or additionally, the second WiFi messages of the third aspect may include power plug status data that may be indicative of whether a power plug of the second patient bed may be plugged into a power receptacle and building the second signal strength profile of the third aspect may occur only if the power plug status data indicates that the power plug of the second patient bed may be plugged into the power receptacle. Further alternatively or additionally, the second WiFi messages of the third aspect may include caster brake status data that may be indicative of whether one or more casters of the second patient bed may be braked or released and building the second signal strength profile of the third aspect may occur only if the caster brake status data indicates that the one or more casters of the second patient bed may be braked.

Optionally, the second WiFi messages of the third aspect may include caster brake status data that may be indicative of whether one or more casters of the second patient bed is braked or released. In such embodiments of the third aspect, building the second signal strength profile may occur only if the caster brake status data indicates that the one or more casters of the second patient bed may be braked.

In some embodiments of the wireless locating method of the third aspect, building the first signal strength profile may include receiving the first WiFi messages over a threshold amount of time and storing in the locating server minimum signal strength values and maximum signal strength values for each wireless access point of the plurality of wireless access points that may be in communication with the first patient bed during the threshold amount of time. In such embodiments, determining that the second signal strength profile may match the first signal strength profile may include determining that the signal strength data in the second WiFi messages for a preset number of WAP's of the plurality of WAP's may be between the respective minimum signal strength values and maximum signal strength values for each of the preset number of WAP's.

If desired, the preset number of WAP's may be less than all of the WAP's in communication with the second patient bed of the third aspect. Alternatively or additionally, the preset number of WAP's may correspond to a set number of WAP's that may have highest signal strength from among the plurality of WAP's that may be in communication with the second patient bed. For example, the set number of the third aspect may be at least four.

It is contemplated by the present disclosure that the wireless locating method of the third aspect may further include filtering out anomalous signal strength data from inclusion in the minimum signal strength values and the maximum signal strength values. For example, the anomalous signal strength data may include signal strength data that may be below a predetermined signal strength threshold.

If desired, the wireless locating method of the third aspect may further include initiating from the locating server a recalibration request to have the location ID re-entered manually with the GUI of the first patient bed if one or more of the signal strengths of the first WiFi messages may be indicative of one or more obstructions being present in the patient room. Alternatively or additionally, initiating from the locating server of the third aspect a recalibration request to have the location ID re-entered manually with the GUI of the first patient bed if one or more of the signal strengths of the first WiFi messages may be indicative that a wireless network including the plurality of WAP's may have been updated. Optionally, the wireless network may be determined to be updated by the locating server in response to one or more WAP's of the plurality of WAP's being removed from the wireless network. Further optionally, the wireless network may be determined to be updated by the server in response to one or more additional WAP's being added to the wireless network.

The present disclosure further contemplates a system for carrying out the method of the third aspect and the system may have any of the features set forth above in any one or more of the preceding sentences pertaining to the third aspect. As such, the system of the third aspect may include one or more of the following: the locating server, the first patient bed, the plurality of WAP's, and the second patient bed. The present disclosure also contemplates a nontransitory computer-readable medium having instructions stored thereon for carrying out the method of any of the features set forth in any one or more of the preceding sentences pertaining to the third aspect.

According to a fourth aspect of the present disclosure, a wireless locating method may include entering a location identification (ID) on a user interface (UI) of a first piece of equipment that may have manual location ID entry capability. The location ID may correlate to a building location at which the first piece of equipment may be located. The method of the fourth aspect may include transmitting from the first piece of equipment first wireless fidelity (WiFi) messages that may include the location ID and a first equipment ID for receipt by a plurality of wireless access points (WAP's) of a computer network of a building. The method of the fourth aspect may further include determining signal strengths of the first WiFi messages that may be received at each of the WAP's of the plurality of WAP's. Furthermore, the method of the fourth aspect may include storing the signal strengths of the first WiFi messages as a first signal strength profile in memory of a locating server. The first signal strength profile may be indicative of the building location in which the first piece of equipment may be located. The method of the fourth aspect may further include removing the first piece of equipment from the building location and transporting a second piece of equipment to the building location. The second piece of equipment may lack manual location ID entry capability. Additionally, the method of the fourth aspect may also include transmitting from the second piece of equipment second WiFi messages that may include a second equipment ID for receipt by the plurality of WAP's of the computer network of the building. The method of the fourth aspect still further may include determining signal strengths of the second WiFi messages that may be received at each of the WAP's of the plurality of WAP's, storing the signal strengths of the second WiFi messages as a second signal strength profile in memory of the locating server, and comparing the second signal strength profile with the first signal strength profile. If the second signal strength profile substantially matches the first signal strength profile, the method of the fourth aspect may include determining by the locating server that the second piece of equipment may be located at the building location.

In some embodiments of the fourth aspect, the first WiFi messages may include power plug status data that may be indicative of whether a power plug of the first piece of equipment may be plugged into a power receptacle. Optionally, storing the signal strengths of the first WiFi messages as the first signal strength profile may occur only if the power plug status data indicates that the power plug of the first piece of equipment may be plugged into the power receptacle. Further optionally, the second WiFi messages may include power plug status data that may be indicative of whether a power plug of the second piece of equipment may be plugged into a power receptacle. If desired, storing the signal strengths of the second WiFi messages as the second signal strength profile may occur only if the power plug status data indicates that the power plug of the second piece of equipment may be plugged into the power receptacle.

In some embodiments of the wireless locating method of the fourth aspect, storing the signal strengths of the first WiFi messages as the first signal strength profile may include receiving the first WiFi messages over a threshold amount of time and storing in the server minimum signal strength values and maximum signal strength values for each WAP of the plurality of WAP's that may be in communication with the first piece of equipment. In such embodiments, determining that the second signal strength profile may match the first signal strength profile may include determining that the signal strengths of the second WiFi messages for a preset number of WAP's of the plurality of WAP's may be between the respective minimum signal strength values and maximum signal strength values for each of the preset number of WAP's.

If desired, the preset number of WAP's may be less than all of the WAP's that may be in communication with the second piece of equipment. Alternatively or additionally, the preset number of WAP's may correspond to a set number of WAP's that may have highest signal strength from among the plurality of WAP's that may be in communication with the second piece of equipment. For example, the set number is at least four.

It is contemplated by the present disclosure that the wireless locating method of the fourth aspect may further include filtering out anomalous signal strengths of the first WiFi messages from inclusion in the minimum signal strength values and the maximum signal strength values. For example, the anomalous signal strengths of the first WiFi messages may include signal strengths being below a predetermined signal strength threshold.

If desired, the wireless locating method of the fourth aspect may further include initiating from the locating server a recalibration request to have the equipment ID re-entered manually with the UI of the first piece of equipment if the signal strengths of the first WiFi messages may be indicative of one or more obstructions being present at the first location. Alternatively or additionally, initiating from the locating server a recalibration request to have the equipment ID re-entered manually with the UI of the first piece of equipment if the signal strengths of the first WiFi messages may be indicative that a wireless network including the plurality of WAP's may have been updated. Optionally, the wireless network may be determined to be updated by the server in response to one or more WAP's of the plurality of WAP's being removed from the wireless network. Further optionally, the wireless network may be determined to be updated by the server in response to one or more additional WAP's being added to the wireless network.

The present disclosure further contemplates a system for carrying out the method of the fourth aspect and the system may have any of the features set forth above in any one or more of the preceding sentences pertaining to the fourth aspect. As such, the system of the fourth aspect may include one or more of the following: the locating server, the first piece of equipment, the plurality of WAP's, and the second piece of equipment. The present disclosure also contemplates a nontransitory computer-readable medium having instructions stored thereon for carrying out the method of any of the features set forth in any one or more of the preceding sentences pertaining to the fourth aspect.

According to a fifth aspect of the present disclosure, a wireless locating method may include receiving first location messages at a server. The first location messages may include bed identification (ID) data of a first hospital bed that may be connected via a wired connection to a location unit that may be mounted in a first location. The first location messages also may include location data that may be transmitted from the location unit and that may correlate to the first location. The method of the fifth aspect may also include receiving first access point messages that may include signal strength data from a plurality of wireless access points that may be in wireless communication with the first patient bed. The first access point messages of the fifth aspect also may include bed ID data that may be transmitted wirelessly from the first patient bed. The method of the fifth aspect may further include using the bed ID data at the server to associate the first access point messages with the first location messages. Still further, the method of the fifth aspect may include building with the server a first signal strength profile for the first location. The first signal strength profile of the fifth aspect may be based on the signal strength data that may be contained in the first signal strength messages. The method of the fifth aspect may also include receiving second messages at the server. The second messages of the fifth aspect may be devoid of any location data from the location unit and the second messages may include signal strength data from the wireless access points that may be in communication with a second patient bed which may lack any wired connection to the location unit. The second messages of the fifth aspect also may include second bed ID data that may be transmitted wirelessly from the second patient bed. The method of the fifth aspect still further may include building with the server a second signal strength profile that may be based on the signal strength data that may be contained in the second messages, comparing with the server the second signal strength profile with the first signal strength profile, and determining with the server that the second patient bed may be at the first location if the second signal strength profile matches the first signal strength profile.

In some embodiments of the fifth aspect, the first messages may include caster brake status data that may be indicative of whether one or more casters of the first patient bed may be braked or released and building the first signal strength profile may occur only if the caster brake status data may indicate that the one or more casters of the first patient bed may be braked. Optionally, the second messages of the fifth aspect may include power plug status data that may be indicative of whether a power plug of the second patient bed may be plugged into a power receptacle and building the second signal strength profile may occur only if the power plug status data may indicate that the power plug of the second patient bed may be plugged into the power receptacle. Further optionally, the second messages of the fifth aspect may include caster brake status data that may be indicative of whether one or more casters of the second patient bed may be braked or released and building the second signal strength profile may occur only if the caster brake status data indicates that the one or more casters of the second patient bed may be braked.

If desired, the second messages of the fifth aspect may include caster brake status data that may be indicative of whether one or more casters of the second patient bed may be braked or released and building the second signal strength profile may occur only if the caster brake status data indicates that the one or more casters of the second patient bed may be braked.

In some embodiments of the wireless locating method of the fifth aspect, building the first signal strength profile may include receiving the first messages over a threshold amount of time and storing in the server minimum signal strength values and maximum signal strength values for each wireless access point of the plurality of wireless access points that may be in communication with the first patient bed during the threshold amount of time. In such embodiments, determining that the second signal strength profile of the fifth aspect matches the first signal strength profile may include determining that the signal strength data in the second messages for a preset number of wireless access points of the plurality of wireless access points may be between the respective minimum signal strength values and maximum signal strength values for each of the preset number of wireless access points.

If desired, the preset number of wireless access points may be less than all of the wireless access points that may be in communication with the second patient bed. Alternatively or additionally, the preset number of wireless access points may correspond to a set number of wireless access points that may have highest signal strength from among the plurality of wireless access points that may be in communication with the second patient bed. For example, the set number may be at least four.

It is contemplated by the present disclosure that the wireless locating method of the fifth aspect may further include filtering out anomalous signal strength data from inclusion in the minimum signal strength values and the maximum signal strength values. For example, the anomalous signal strength data of the fifth aspect may include signal strength data that may be below a predetermined signal strength threshold.

If desired, the wireless locating method of the fifth aspect further may include initiating from the server a recalibration request to have the bed location data re-entered manually with the user interface of the first patient bed if the signal strength data of the first messages may be indicative of one or more obstructions being present at the first location. Alternatively or additionally, the method of the fifth aspect may further include initiating from the server a recalibration request to have the bed location data re-entered manually with the user interface of the first patient bed if the signal strength data of the first messages may be indicative that a wireless network including the plurality of wireless access points may have been updated. Optionally, the wireless network may be determined to be updated by the server in response to one or more wireless access points of the plurality of wireless access points being removed from the wireless network. Further optionally, the wireless network may be determined to be updated by the server in response to one or more additional wireless access points being added to the wireless network.

The present disclosure further contemplates a system for carrying out the method of the fifth aspect and the system may have any of the features set forth above in any one or more of the preceding sentences pertaining to the fifth aspect. As such, the system of the fifth aspect may include one or more of the following: the server, the first patient bed, the plurality of wireless access points, and the second patient bed. The present disclosure also contemplates a nontransitory computer-readable medium that may have instructions stored thereon for carrying out the method of any of the features set forth in any one or more of the preceding sentences pertaining to the fifth aspect.

According to a sixth aspect of the present disclosure, a wireless locating method may include receiving first location messages at a server. The first location messages may include first equipment identification (ID) data of a first piece of equipment that may be connected via a wired connection to a location unit that may be mounted in a first location. The first location messages also may include location data that may be transmitted from the location unit and that may correlate to the first location. The method of the sixth aspect may also include receiving first access point messages that may include signal strength data from a plurality of wireless access points that may be in wireless communication with the first piece of equipment. The first access point messages of the fifth aspect also may include the first equipment ID data that may be transmitted wirelessly from the first piece of equipment. The method of the sixth aspect may further include using the first equipment ID data at the server to associate the first access point messages with the first location messages. Still further, the method of the sixth aspect may include building with the server a first signal strength profile for the first location. The first signal strength profile of the sixth aspect may be based on the signal strength data that may be contained in the first signal strength messages. The method of the sixth aspect may also include receiving second access point messages at the server. The second access point messages may include signal strength data from the wireless access points that may be in communication with a second piece of equipment which may lack any wired connection to the location unit. The second access point messages of the sixth aspect also may include second equipment ID data that may be transmitted wirelessly from the second piece of equipment. The method of the sixth aspect still further may include building with the server a second signal strength profile that may be based on the signal strength data that may be contained in the second access point messages, comparing with the server the second signal strength profile with the first signal strength profile, and determining with the server that the second piece of equipment may be at the first location if the second signal strength profile matches the first signal strength profile.

In some embodiments of the sixth aspect, the second messages may include power plug status data that may be indicative of whether a power plug of the second piece of equipment may be plugged into a power receptacle and building the second signal strength profile may occur only if the power plug status data indicates that the power plug of the second piece of equipment may be plugged into the power receptacle. Optionally, building the first signal strength profile of the sixth aspect may include receiving the first messages over a threshold amount of time and storing in the server minimum signal strength values and maximum signal strength values for each wireless access point of the plurality of wireless access points that may be in communication with the first piece of equipment.

If desired, determining that the second signal strength profile matches the first signal strength profile may include determining that the signal strength data in the second messages for a preset number of wireless access points of the plurality of wireless access points may be between the respective minimum signal strength values and maximum signal strength values for each of the preset number of wireless access points. Optionally, the preset number of wireless access points of the sixth aspect may be less than all of the wireless access points that may be in communication with the second piece of equipment. Further optionally, the preset number of wireless access points of the sixth aspect may correspond to a set number of wireless access points that may have highest signal strength from among the plurality of wireless access points that may be in communication with the second piece of equipment. For example, the set number of the sixth aspect may be at least four.

In some embodiments, the wireless locating method of the sixth aspect may further include filtering out anomalous signal strength data from inclusion in the minimum signal strength values and the maximum signal strength values. For example, the anomalous signal strength data of the sixth aspect may include signal strength data that may be below a predetermined signal strength threshold.

If desired, the wireless locating method of the sixth aspect further may include initiating from the server a recalibration request to have the equipment location data re-entered manually with the user interface of the first piece of equipment if the signal strength data of the first messages may be indicative of one or more obstructions being present at the first location. Alternatively or additionally, the sixth aspect may include initiating from the server a recalibration request to have the equipment location data re-entered manually with the user interface of the first piece of equipment if the signal strength data of the first messages may be indicative that a wireless network including the plurality of wireless access points may have been updated. Optionally, the wireless network of the sixth aspect may be determined to be updated by the server in response to one or more wireless access points of the plurality of wireless access points being removed from the wireless network. Further optionally, the wireless network of the sixth aspect may be determined to be updated by the server in response to one or more additional wireless access points being added to the wireless network.

The present disclosure further contemplates a system for carrying out the method of the sixth aspect and the system may have any of the features set forth above in any one or more of the preceding sentences pertaining to the sixth aspect. As such, the system of the sixth aspect may include one or more of the following: the server, the first piece of equipment, the plurality of wireless access points, and the second piece of equipment. The present disclosure also contemplates a nontransitory computer-readable medium that may have instructions stored thereon for carrying out the method of any of the features set forth in any one or more of the preceding sentences pertaining to the sixth aspect.

Additional features, which alone or in combination with any other feature(s), such as those listed above and those listed in the claims, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIGS. 3A-3C form a flow chart of a method for determining that the second patient bed has been moved into the first patient room by comparing signal strength profiles based on signal strength information from the WAP's as received from the first and second patient beds;

FIG. 4 is a table of data corresponding to a first signal strength profile for the first patient bed when located in the first patient room;

FIG. 5 is a table of data corresponding to a second signal strength profile for the second patient bed when located in the first patient room;

DETAILED DESCRIPTION

In the description that follows, a system 10 is disclosed for determining locations of patient support apparatuses, such as patient beds, in a healthcare facility. However, the locating systems and methods disclosed herein may be used in healthcare facilities to locate other pieces of equipment such as infusion pumps, vital signs monitors such as electrocardiograms (EKG's), mobile patient lifts, mobile imaging equipment, passive motion devices, motorized wheelchairs, surgical tables, and the like. Furthermore, the principles of the present disclosure are also applicable to determining locations of pieces of equipment in environments other than healthcare facilities. For example, the locating systems and methods disclosed herein may be used for locating mobile manufacturing equipment in a manufacturing facility, office equipment in an office environment, and other pieces of equipment in their respective in-door environments. Thus, in the description that follows, reference is made to a first patient bed and a second patient bed but the description is equally applicable to a first piece of equipment and a second piece of equipment unless specifically noted otherwise (e.g., the discussion clearly pertains only to patient beds). Furthermore, in FIGS. 3A-5 the text "BED 1" and "BED 2" may just as well have "EQUIPMENT 1" and "EQUIPMENT 2" substituted therefor, because the principles disclosed in these FIGS. are equally applicable to beds and to generic equipment.

Figure 1:
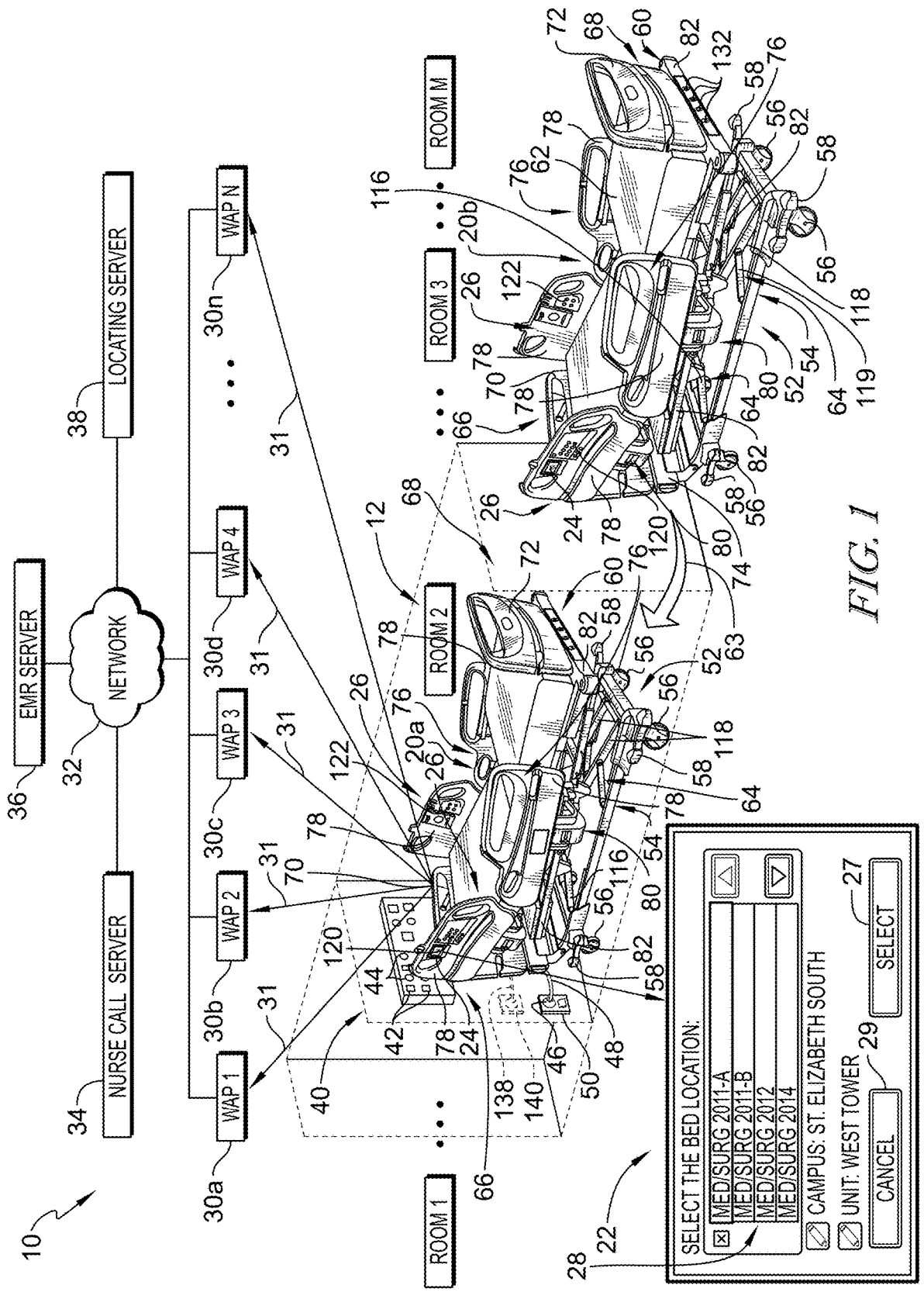
FIG. 1 is a diagrammatic view showing a first patient bed in a first patient room communicating via wireless fidelity (WiFi) signals with multiple wireless access points (WAP's) of a network of a healthcare facility, the first patient bed having a graphical user interface for manual entry of a location identification (ID) corresponding to the first patient room, and a second patient bed that can be moved into the first patient room after the first patient bed is removed from the patient room.

As shown diagrammatically in FIG. 1, system 10 includes a first patient bed 20a located in a first patient room 12, illustratively designated as ROOM 2 from among a series of patient rooms designated as ROOM 1 through ROOM M. Bed 20a is configured with capability for a caregiver to manually select the name of the patient room 12 or location in which bed 20a is located as indicated by a location selection screen 22 which is enlarged in FIG. 1. Screen 22 appears on a graphical user interface (GUI) 24 mounted on one of a pair of head end siderails 26 of bed 20a in the illustrated embodiment. Screen 22 includes a menu or table 28 of the bed locations (e.g., room names) that are selectable for association with bed 20a. For example, the list of bed locations in table 28 may correspond to the rooms of a particular unit, wing, or ward of the healthcare facility such as a hospital, outpatient care facility, nursing home, and the like.

After the caregiver selects the particular bed location (aka room location or simply just location) on table 28, the caregiver touches select button 27 to store the bed location in memory of bed 20a. Thus, in the illustrative example, the caregiver selects the bed location on table 28 of screen 22 that corresponds to room 12 which is diagrammatically labeled in FIG. 1 as ROOM 2. A cancel button 29 is provided on screen 22 if the caregiver decides not to manually associate bed 20a with any of the bed locations, such as room 12, on table 28. Additional details of the manual location selection capability of bed 20a can be found in U.S. application Ser. No. 16/743,340, filed Jan. 15, 2020, titled "Bed Interface for Manual Location," and which is hereby incorporated by reference herein in its entirety for all that it teaches to the extent not inconsistent with the present disclosure which shall control as to any inconsistencies.

Still referring to FIG. 1, bed 20a is further equipped with the capability of communicating via wireless fidelity (WiFi) signals with multiple wireless access points (WAP's) 30a, 30b, 30c, 30d, 30n of a network 32 of system 10 of the respective healthcare facility as indicated diagrammatically by arrows 31. In FIG. 1, the letter "M" of the ROOM M block and the letter "N" of the WAP N 30n block is intended to indicate that system 10 includes any number of rooms and any number of WAP's and that the number of rooms and the number of WAP's need not be the same number, but that is not to exclude such a possibility. System 10 further includes multiple servers, such as illustrative nurse call server 34, electronic medical record (EMR) server 36, and locating server 28 that are communicatively coupled to each other via network 32. Network 32 may include any number of other servers as well, such as an admission/discharge/transfer (ADT) server, communication server, and so forth.

The "cloud" block 32 of system 10 is intended to represent various other portions of the network infrastructure of the healthcare facility not included in the depicted portions (e.g., WAP's 30a-30n and servers 34, 36, 38). Thus, network 32 is intended to represent such network infrastructure as Ethernet jacks such as RJ-45 connectors, wires, routers, gateways, voice over Internet protocol (VOIP) switches, and the like provided in a healthcare facility as well as the various computer devices such as personal computers, other servers, laptop computers, computerized patient care equipment, mobile communication devices (e.g., wireless phones) that are coupled to the network infrastructure. The various components of system 10 described herein may communicate with each other using portions of network 32. In the illustrative example, WAP's 30a-30n communicate with one or more of servers 34, 36, 38 via portions of network 32.

Figure 2:
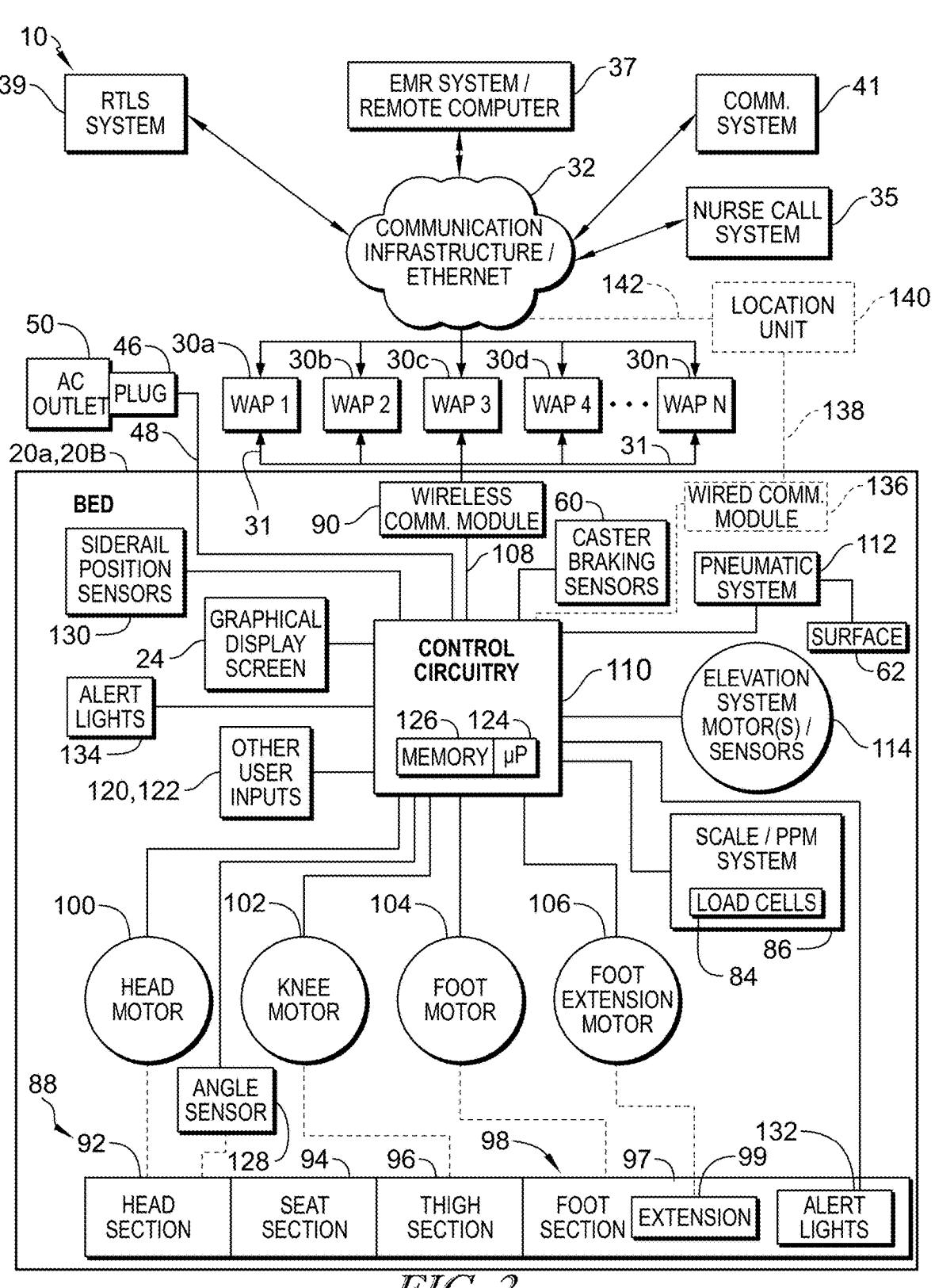
FIG. 2 is a block diagram showing various components of the first and second patient beds of FIG. 1 and also showing components of the network of the healthcare facility.

In FIG. 2, a nurse call system 35, an EMR system/remote computer 37, and real time locating system (RTLS) 39 are shown diagrammatically. It should be appreciated that servers 34, 36, 38 are components of systems 35, 37, 39, respectively. However, the blocks corresponding to systems 35, 37, 39 in FIG. 2 are intended to represent other components of the respective systems 35, 37, 39 as well. For example, in addition to nurse call server 34, nurse call system 35 optionally may include one or more of the following: a master nurse station or computer, an electronic status board in communication with the master nurse station and/or server 34, a plurality of room stations (sometimes referred to as audio stations or graphical audio stations) in the various patient rooms (e.g., ROOMS 1-M) and in communication with the master nurse station, indicator assemblies such as dome lights adjacent the doorways of the various patient rooms, input/output (I/O) boards coupled to the room stations and dome lights, bathroom call switches, shower call switches, and so forth. Further optionally, nurse call system 35 may include computer devices such as desktop computers, laptop computers, computers on wheels (COW's), mobile phones, and personal digital assistants that are communicatively coupled to nurse call server 34 for receiving nurse call information such as nurse calls, bed status data, bed alerts, and/or other alerts from nurse call system 35 for display on the associated display screens of the various computer devices. Additional details of components included in a nurse call system can be found in U.S. Pat. Nos. 8,598,995; 8,384,526; 8,169,304; 8,046,625 and 7,319,386; each of which is hereby incorporated by reference herein to the extent not inconsistent with the present disclosure which shall control as to any inconsistencies.

In addition to EMR server 36, embodiments of EMR system 37 optionally may include additional computer devices such as one or more of the following: desktop computers, laptop computers, computers on wheels (COW's), mobile phones, and personal digital assistants that are communicatively coupled to EMR server 36 and that are configured for entering data into EMR system 37 and retrieving data from EMR system 37 for viewing on the associated display screens of these various computer devices. In addition to locating server 38, the RTLS 39 optionally may include locating tags attached to patients, caregivers, and/or equipment, receivers or transceivers in communication with the locating tags, and computer devices such as desktop computers, laptop computers, computers on wheels (COW's), mobile phones, and personal digital assistants that are communicatively coupled to locating server 38 for retrieving locating information from the RTLS 39 for display on the associated display screens of the various computer devices. However, it should be understood that beds 20a, 20b are not located within system 10 by use of locating tags but other people and equipment may be in some embodiments.

It is contemplated by the present disclosure that some computer devices may be included as part of the nurse call system 35 and/or the EMR system 37 and/or the RTLS 39. For example, a desktop computer or mobile phone may be communicatively coupled to two or three of systems 35, 37, 39, as well as to other systems of the healthcare facility. A communication system 41 is also shown in FIG. 2 as being included in system 10 and coupled to network 32. Communication system 41 may include, for example, one or more communication servers such as a VOIP server and/or a text message server, as well as other equipment such as a digital branch exchange (DBX), private branch exchange (PBX), VOIP switches, wired telephones, mobile phones, and the like. Some components of system 41 facilitate the routing of communications between the various computer devices (e.g., computers and mobile phones) of systems 35, 37, 39.

In FIGS. 1 and 2, communication links between various portions of system 10 are depicted by single headed arrows, double headed arrows, solid lines, and dashed lines. These various communication link depictions are each intended to represent bidirectional communication links between the interconnected portions of system 10 unless specifically noted otherwise. Furthermore, the communication links depicted in FIGS. 1 and 2 include wired communication links or wireless communication links or both at the option of the designer of system 10 in any given healthcare facility, unless specifically noted otherwise. For example, communication links 31 between beds 20a, 20b and WAP's 30a-30n are each WiFi links (e.g., according to any of the 802.11x protocols). However, other wireless communication between the other portions of system 10 contemplated by this disclosure may optionally include: Bluetooth (BT), Bluetooth Low Energy (BLE), Zigbee, Z-Wave, and WiFi (e.g., any of the 802.11x protocols). However, this is not rule out other types of wireless communication including infrared (IR) communications, ultrasonic (US) communications, ultra-wideband (UWB) communications, and so forth.

Referring once again to FIG. 1, after the bed location is selected on menu 28 of screen 22, the bed location information is stored as bed location data (aka location identification (ID) information or data) in memory of bed 20a and thereafter, the bed location data is transmitted periodically along with other bed status data or information as WiFi messages. Some or all of the WAP's 30a-30n receive the WiFi messages from bed 20a and determine the signal strength (e.g., received signal strength indicator (RSSI)) of the received messages. The WAP's 30a-30n receiving the WiFi messages from bed 20a, in turn, transmit the data contained in those messages, including the bed location data, along with data indicative of the signal strengths of the WiFi messages received from bed 20a to one or more of servers 34, 36, 38. For example, the data contained in the WiFi messages may be transmitted for receipt by nurse call server 34 and then server 34 may transmit some or all of the received data to server 36 and/or sever 38.

The present disclosure contemplates that the bed location data from bed 20a and the signal strength data from the WAP's 30a-30n receiving the bed location data is ultimately transmitted to locating server 38 for storage in a database of server 38. The bed location data and signal strength data is used by server 38 to build a signal strength profile for bed 20*a* when located in room 12, designated by the block labeled ROOM 2. Aspects of the signal strength profile will be discussed in further detail below. The signal strength profile may be created by server 38 based on the messages received from bed 20*a* by the one or more WAP's 30*a*-30*n* for a predetermined period of time (e.g., 5 minutes, 10 minutes, 2 hours, 4 hours, 8 hours, etc.) or based on the messages received from bed 20*a* for the entirety of the time that bed 20*a* is located in room 12 and is generally stationary.

Still referring to FIG. 1, room 12 has a headwall unit 40 that includes various medical service outlets such as electrical outlets 42 and gas outlets 44. When a patient bed, such as bed 20*a*, is transported to room 12 it is placed in room 12 with its head end situated in relatively close proximity (e.g., about 6 inches to about 18 inches) of head wall unit 40 and is generally centered with respect to head wall unit 40. It is contemplated by the present disclosure that each of ROOMS 1-M have a head wall unit 40 or something like a head wall unit 40 (e.g., a bed locator unit, a service chase, or the like) within the respective room to designate the particular place within the room that a patient bed should be located. In other words, when one bed in each of the patient rooms is replaced with another bed, the beds are positioned within the rooms at the same general locations (e.g., within about 6 inches to about 18 inches).

With regard to determining that a patient bed, such as bed 20*a*, is stationary in a particular room, such as room 12, particular pieces of bed data may be used by server 34 and/or server 38 to make this determination. For example, bed 20*a* is shown in FIG. 1 with a power plug 46 at an end of a power cable 48 of bed 20*a* plugged into a power receptacle 50, such as a standard alternating current (AC) outlet, of room 12. Thus, while bed 20*a* is plugged in to receptacle 50, it can generally be assumed that bed 20*a* is going to be relatively stationary and is not going to be moved to another location. Accordingly, among the bed data included in the WiFi messages from bed 20*a* is power plug status data indicative of whether bed 20*a* is receiving power from a power outlet, such as outlet 50, via plug 46 and cable 48.

In some embodiments, caster brake status data is used by server 34 and/or server 38 in addition to, or in lieu of, the power plug status data to determine that bed 20*a* is stationary. Bed 20*a* includes a frame 52 which, in turn, includes a base frame 54 to which a set of casters 56 are coupled to provide for maneuverability and transport of bed 20*a* along a floor. Bed 20*a* further includes foot pedals 58 that are used to brake and release one or more of casters 56. Thus, in one position of foot pedals 58 casters 56 are braked and in another position of pedals 58, casters 56 are unbraked or released.

Various types of releaseable brakes for casters 56 are known in the art including plunger style caster brakes in which a plunger is pressed against a resilient tread of the wheels of one or more of casters 56 to prevent the caster wheels from rolling and clutch or lever style caster brakes in which a clutch or lever engages a portion of the hub of the wheels of one or more of casters 56 to prevent the caster wheels from rolling. In any event, bed 20*a* includes one or more caster braking sensors 60, shown diagrammatically in FIG. 2, such as limit switches, Hall effect sensors, and the like, to sense whether casters 56 are braked or released. Thus, while one or more of casters 56 of bed 20*a* are braked, it can generally be assumed that bed 20*a* is going to be relatively stationary and is not going to be moved to another location. Accordingly, among the bed data included in the WiFi messages from bed 20*a* is caster brake status data indicative of whether one or more of casters 56 of bed 20*a* are braked.

After bed 20*a* has been situated in room 12 in a stationary state for some period of time such that a signal strength profile has been created in server 38 for bed 20*a* in room 12, bed 20*a* is transported out of room 12 and moved to some other location of the healthcare facility such as another one of ROOMS 1-M or to a maintenance or storage location of the healthcare facility. In this regard, to move bed 20*a* out of room 12, pedals 58 are operated to unbrake (aka release) the casters 56 and the power plug 46 is unplugged from receptacle 50. Upon detection of the caster releasing and/or unplugging events by server 34 or server 38 based on data in the WiFi messages from bed 20*a* that continue to be transmitted for a period of time by bed 20 under battery power, for example, server 38 ceases to accumulate signal strength data for purposes of building the signal strength profile for bed 20*a* in room 12 in those embodiments in which the signal strength profile is created during the entirety of the duration that bed 20*a* is in room 12 and in a stationary state.

After bed 20*a* is removed from room 12, a second bed 20*b* is moved into room 12 as indicated diagrammatically by arrow 63 in FIG. 1. When bed 20*b* is moved into room 12, it is placed substantially in the same position (e.g., within a foot or so) of the position at which bed 20*a* was placed when in room 12. Thus, bed 20*b* is positioned within room 12 so that its head end is in proximity to head wall unit 40 and generally centered (e.g., within a foot) relative to the head wall unit 40. In the illustrative example, bed 20*b* is the same type of bed as bed 20*a*, but bed 20*b* lacks the capability to have bed location entered manually on the GUI 24 of bed 20*b*. That is, the manual location ID entry capability of bed 20*a* is an optional feature of bed 20*a* and that feature is omitted from bed 20*b*.

Similar to bed 20*a*, bed 20*b* also has wireless communication capability and therefore, is configured to transmit WiFi messages to one or more of WAP's 30*a*-30*n*. However, the WiFi messages transmitted by bed 20*b* are devoid of any bed location data. Some or all of the WAP's 30*a*-30*n* receive the WiFi messages from bed 20*b* and determine the signal strength of the received messages. The WAP's 30*a*-30*n* receiving the WiFi messages from bed 20*b*, in turn, transmit the data contained in those messages along with data indicative of the signal strengths of the WiFi messages received from bed 20*b* to one or more of servers 34, 36, 38. For example, the data contained in the WiFi messages from bed 20*b* may be transmitted for receipt by nurse call server 34 and then server 34 may transmit some or all of the received data to server 36 and/or sever 38.

The signal strength data from the WAP's 30*a*-30*n* receiving the bed data from bed 20*b* is ultimately transmitted to locating server 38 for storage in a database of server 38. The signal strength data associated with the WiFi messages from bed 20*b* is used by server 38 to build a signal strength profile for bed 20*b* in a similar manner that the signal strength profile was built for bed 20*a*. However, at the initial stages of building the signal strength profile for bed 20*b*, the location of bed 20*b* has not yet been determined by server 38. The signal strength profile may be created by server 38 based on the messages received from bed 20*b* by the one or more WAP's 30*a*-30*n* for a predetermined period of time (e.g., 5 minutes, 10 minutes, 2 hours, 4 hours, 8 hours, etc.) if it is determined that bed 20*b* is generally stationary. In this regard, power plug status data and/or caster brake status data for bed 20*b* as contained in the WiFi messages from bed 20*b* is used by server 34 and/or server 38 to make the determination that bed 20*b* is generally stationary as was discussed above in connection with bed 20*a*.

After the signal strength profile for bed 20*b* has been built, server 38 compares the bed 20*b* signal strength profile with those that have been created previously for each of ROOMS 1-M. If server 38 determines that the signal strength profile of bed 20*b* matches the signal strength profile for a particular room, then server 38 determines that bed 20*b* is in the particular room having the signal strength profile match. In the illustrative example, therefore, server 38 determines that bed 20*b* is in room 12 as a result of the signal strength profile created for bed 20*b* matching the signal strength profile of bed 20*a* that was created previously when bed 20*a* was located in room 12. The circumstances under which two signal strength profiles are considered to be a "match" is discussed in further detail below.

As alluded to above, the present disclosure is primarily focused on bed-to-room association based on the use of signal strength profiles of WiFi communications between patient beds and wireless access points. However, a discussion is provided below of the basic components and operation of various features of illustrative beds 20*a*, 20*b* so that an understanding of the types of bed status data transmitted wirelessly by beds 20*a*, 20*b* to one or more of WAP's 30*a*-30*n* can be gained. Illustrative beds 20*a*, 20*b* depicted in FIG. 1 are each the CENTRELLA® bed available from Hill-Rom Company, Inc. Other aspects of illustrative beds 20*a*, 20*b* are shown and described in more detail in U.S. Patent Application Publication No. 2018/0161225 A1 which is hereby expressly incorporated by reference herein to the extent not inconsistent with the present disclosure which shall control as to any inconsistencies. However, this disclosure is applicable to other types of patient support apparatuses having other configurations, including other types of beds, surgical tables, examination tables, stretchers, chairs, wheelchairs, patient lifts and the like.

As noted above, beds 20*a*, 20*b* each include a patient support structure such as frame 52 that, in turn, includes a base frame 54 and casters 56. Frame 52 further includes an upper frame assembly 60 that supports a surface or mattress 62 as shown in FIG. 1. Frame 52 of each of beds 20*a*, 20*b* further includes a lift system 64 coupling upper frame assembly 60 to base frame 54. Lift system 64 is operable to raise, lower, and tilt upper frame assembly 60 relative to base frame 54. Each bed 20*a*, 20*b* has a head end 66 and a foot end 68. Beds 20*a*, 20*b* each further include a headboard 70 at the head end 66 a footboard 72 at the foot end 68. Headboard 70 is coupled to an upstanding portion 74 of base frame 54 and footboard 72 is coupled to upper frame assembly 60.

Illustrative patient beds 20*a*, 20*b* each have four siderail assemblies coupled to upper frame assembly 60 as shown in FIG. 1. The four siderail assemblies include the pair of head end siderails 26 (sometimes referred to as head rails) and a pair of foot end siderails 76 (sometimes referred to as foot rails). Each of the siderail assemblies 26 and 76 is movable between a raised position, as shown in FIG. 1, and a lowered position (not shown, but well-known in the art. Each siderail 26, 76 includes a barrier panel 78 and a linkage 80. Each linkage 80 is coupled to the upper frame assembly 60 and is configured to guide the respective barrier panel 78 during movement of siderails 26, 76 between the respective raised and lowered positions. Barrier panels 78 are each maintained by the linkage 80 in a substantially vertical orientation during movement of siderails 26, 76 between the respective raised and lowered positions.

Upper frame assembly 60 includes various frame elements 82, shown in FIG. 1, that form, for example, a lift frame and a weigh frame supported with respect to the lift frame by a set of load cells 84 of a scale and/or bed exit/patient position monitoring (PPM) system 86 of beds 20*a*. 20*b*, shown diagrammatically in FIG. 2. A patient support deck 88, shown diagrammatically in FIG. 2, is carried by the weigh frame portion of upper frame assembly 60 and supports mattress 62 thereon. Data relating to the operation of the scale and/or bed exit/PPM system 86 is among the features of beds 20*a*, 20*b* for which bed status data is transmitted wirelessly from a wireless communication module 90, shown diagrammatically in FIG. 2, to one or more of WAP's 30*a*-30*n*. More particularly, wireless communication module 90 sends WiFi signals or transmissions to one or more WAP's 30*a*-30*n* and, in some embodiments, receives WiFi signals or transmissions from one of more WAP's 30*a*-30*n*. Thus, wireless communication module 90 includes a transmitter and/or a receiver and/or a transceiver in some embodiments. Some or all of these components may be included in a WiFi chipset, for example. Module 90, therefore, includes electrical components such as one or more antennas, amplifiers, resistors, capacitors, integrated circuit chips, and the like.

In some embodiments contemplated by this disclosure, beds 20*a*, 20*b* are manufactured so as to include module 90 therein and in other embodiments, module 90 is contained in a housing that separately mounts to bed 20*a* or bed 20*b* as an optional add-on component. If module 90 is provided as a separate add-on component, cable 108 from module 90 couples to a port of control circuitry 110 that is dedicated for the module 90, but that otherwise remains dormant when module 90 is not present on bed 20*a*, 20*b*. In any event, the communication of data from module 90 is among the features of bed 20*a*, 20*b* controlled by the bed operating software of the respective control circuitry 110.

In some embodiments in which module 90 is integrated into bed 20*a* or bed 20*b* at the time of manufacture, module 90 includes a Model No. VAR-SOM-SOLO: NXP i.M6 Solo device available from Variscite Ltd. of Lod, Israell. The VAR-SOM-SOLO: NXP i.M6 Solo device is configured for Wi-Fi 802.11b/g/n communications and Bluetooth 4.1/BLE communications and features an NXP i.MX6 1 GHz Cortex-A9 processor available from NXP Semiconductors Netherlands B.V. of Eindhoven, Netherlands. In some embodiments in which module 90 is an optional add-on component of bed 20*a* or bed 20*b*, module 90 includes a Model No. WB45NBT device available from Laird Technologies of Earth City, Mo.

Module 90 connects to control circuitry 110 of beds 20*a*, 20*b* via a cable 108 such as a universal serial bus (USB) cable in some embodiments as shown diagrammatically in FIG. 2. In such embodiments, therefore, module 90 and control circuitry 110 each include a port for connection to mating connectors at the ends of cable 108. It is within the scope of the present disclosure, however, for module 90 and circuitry 110 to communicate wirelessly in variant embodiments of beds 20*a*, 20*b*. Module 90 includes a WiFi antenna and, optionally, a Bluetooth (BT) antenna in some embodiments.

Patient support deck 88 includes a head section 92, a seat section 94, a thigh section 96, and a foot section 98 in the illustrative example as shown diagrammatically in FIG. 2. Sections 92, 96, 98 are each movable relative to the weigh frame portion of upper frame assembly 60. For example, head section 92 pivotably raises and lowers relative to seat section 94 whereas foot section 98 pivotably raises and lowers relative to thigh section 96. Additionally, thigh section 96 articulates relative to seat section 94. Also, in some embodiments, foot section 98 is extendable and retractable to change the overall length of foot section 98 and therefore, to change the overall length of deck 88. For example, foot section 98 includes a main portion 97 and an extension 99 in some embodiments as shown diagrammatically in FIG. 2.

In the illustrative embodiment of beds 20a, 20b, seat section 94 is fixed in position with respect to the weigh frame portion of upper frame assembly 60 as patient support deck 88 moves between its various patient supporting positions including a horizontal position to support the patient in a supine position, for example, and a chair position (not shown) to support the patient in a sitting up position. In other embodiments, seat section 94 also moves relative to upper frame assembly 60, such as by pivoting and/or translating. Of course, in those embodiments in which seat section 94 translates relative to the upper frame assembly 60, the thigh and foot sections 96, 98 also translate along with seat section 94. As bed 20a or bed 20b moves from the horizontal position to the chair position, foot section 98 lowers relative to thigh section 96 and shortens in length due to retraction of the extension 99 relative to main portion 97. As bed 20a or bed 20b moves from the chair position to the horizontal position, foot section 98 raises relative to thigh section 96 and increases in length due to extension of the extension 99 relative to main portion 97. Thus, in the chair position, head section 92 extends upwardly from upper frame assembly 60 and foot section 98 extends downwardly from thigh section 96.

As shown diagrammatically in FIG. 2, each of beds 20a, 20b includes a head motor or actuator 100 coupled to head section 92, a knee motor or actuator 102 coupled to thigh section 96, a foot motor or actuator 104 coupled to foot section 98, and a foot extension motor or actuator 106 coupled to foot extension 99. Motors 100, 102, 104, 106 may include, for example, an electric motor of a linear actuator. In those embodiments in which seat section 94 translates along upper frame assembly 50 as mentioned above, a seat motor or actuator (not shown) may also be provided although, in some embodiments, such a motor may not be needed if the seat section 94 is anchored to head section 92 and translates along upper frame assembly 60 along with a lower end of the head section 92 during pivoting movement of head section 92.

Head motor 100 is operable to raise and lower head section 92, knee motor 102 is operable to articulate thigh section 96 relative to seat section 94, foot motor 104 is operable to raise and lower foot section 98 relative to thigh section 96, and foot extension motor 106 is operable to extend and retract extension 99 of foot section 98 relative to main portion 97 of foot section 98. Data relating to the operation of motors 100, 102, 104, 106 and the positions of deck sections 92, 94, 96, 98 is among the features of beds 20a, 20b for which bed status data is transmitted wirelessly from wireless communication module 90 to one or more of WAP's 30a-30n.

In some embodiments, either or both of beds 20a, 20b include a pneumatic system 112 that controls inflation and deflation of various air bladders or cells of mattress 62. The pneumatic system 112 is represented in FIG. 2 as a single block but that block 112 is intended to represent one or more air sources (e.g., a fan, a blower, a compressor) and associated valves, manifolds, air passages, air lines or tubes, pressure sensors, and the like, as well as the associated electric circuitry, that are typically included in a pneumatic system for inflating and deflating air bladders of mattresses. Operation of pneumatic system 112 is among the features of beds 20a, 20b for which bed status data is transmitted wirelessly from module 90 to one or more WAP's 30a-30n.

As also shown diagrammatically in FIG. 2, lift system 64 of each bed 20a, 20b includes one or more elevation system motors or actuators 114, which in some embodiments, comprise linear actuators with electric motors. Thus, actuators 114 are sometimes referred to herein as motors 114 and operation of the motors 114 is among the features of beds 20a, 20b for which bed status data is transmitted wirelessly from module 90 to one or more WAP's 30a-30n. Alternative actuators or motors contemplated by this disclosure include hydraulic cylinders and pneumatic cylinders, for example. The motors 114 of lift system 64 are operable to raise, lower, and tilt upper frame assembly 60 relative to base frame 54. In the illustrative embodiment, one of motors 114 is coupled to, and acts upon, a set of head end lift arms 116 and another of motors 114 is coupled to, and acts upon, a set of foot end lift arms 118 to accomplish the raising, lowering and tilting functions of upper frame 60 relative to base frame 54. Guide links 119 are coupled to base frame 54 and to lift arms 118 in the illustrative example of beds 20a, 20b as shown in FIG. 1 (reference number 119 shown only in connection with bed 20b due to space constraints in FIG. 1).

Each of siderails 26 includes a first user control panel 120 coupled to the outward side of the associated barrier panel 78. Controls panels 120 include various buttons that are used by a caregiver to control associated functions of beds 20a, 20b. For example, control panel 120 includes buttons that are used to operate head motor 100 to raise and lower the head section 92, buttons that are used to operate knee motor 102 to raise and lower the thigh section 96, and buttons that are used to operate motors 114 to raise, lower, and tilt upper frame assembly 60 relative to base frame 54. In some embodiments, control panel 120 also includes buttons that are used to operate motor 104 to raise and lower foot section 98 and buttons that are used to operate motor 106 to extend and retract foot extension 99 relative to main portion 97. Each of siderails 26 also includes a second user control panel 122 coupled to the inward side of the associated barrier panel 78. Control panels 122 include various buttons that are used by a patient to control associated functions of beds 20a. 20b. In some embodiments, the buttons of control panels 120, 122 comprise membrane switches.

As shown diagrammatically in FIG. 2, control circuitry 110 is electrically coupled to motors 100, 102, 104, 106 and to motors 114 of lift system 64. Control circuitry 110 is sometimes referred to as a "controller." Control circuitry 110 is represented diagrammatically as a single block in FIG. 2, but control circuitry 110 in some embodiments, comprises various circuit boards, electronics modules, and the like that are electrically and communicatively interconnected. Control circuitry 110 includes one or more microprocessors 124 or microcontrollers that execute software to perform the various control functions and algorithms of beds 20a, 20b described herein. Thus, circuitry 110 also includes memory 126 for storing software, variables, calculated values, and the like as is well known in the art. Memory 126 comprises, for example, one or more flash memory banks such as one or more EEPROM's, EPROM's, and the like. In some embodiments, memory 126 is included in the same integrated circuit chip as microprocessor 124.

As also shown diagrammatically in FIG. 2, an "other user inputs" block represents the various user inputs such as buttons of control panels 120, 122, for example, that are used by the caregiver or patient to communicate input signals to control circuitry 110 of beds 20a, 20b to command the operation of the various motors 100, 102, 104, 106, 114 of beds 20a, 20b, as well as commanding the operation of other functions of beds 20a, 20b. Each bed 20a, 20b includes GUI or display screen 24 coupled to a respective siderail 26 as noted above and as shown in FIG. 1. Display screen 24 is coupled to control circuitry 110 as shown diagrammatically in FIG. 2. In some embodiments, two graphical user interfaces 24 are provided and are coupled to respective siderails 26. Alternatively or additionally, one or more graphical user interfaces 24 are coupled to siderails 76 and/or to one or both of the headboard 70 and footboard 72 or to some other portion of bed 20a, 20b such as a support arm assembly extending upwardly from base frame 54 or upper frame assembly 60.

Still referring to FIG. 2, beds 20a, 20b each include various sensors to sense the states or positions of various portions of the respective beds 20a, 20b. In the illustrative example, each of beds 20a, 20b includes an angle sensor 128 coupled to head section 92 to sense an angle of head section elevation (sometimes referred to as the head-of-bed (HOB) angle). Angle sensor 128 includes an accelerometer (single-axis or multi-axis) in some embodiments. In such embodiments, the HOB angle is measured with respect to a horizontal reference axis and/or with respect to a vertical reference axis depending upon the orientation of the accelerometer relative to head section 92 and depending upon the type of accelerometer used. In other embodiments, angle sensor 128 includes a rotary potentiometer which measures the HOB angle between head section 92 and another portion of frame 52 such as one of frame members 82 of upper frame assembly 60. In further embodiments, angle sensor 128 is included in head motor 100 and has an output that correlates to the HOB angle. Motor 100 may include, for example, a shaft encoder, a Hall effect sensor, a rotary potentiometer, or some other sensor which serves as angle sensor 128 of bed 20a, 20b in such embodiments. Similar such sensors are included in elevation system motors 114 in some embodiments and are used to determine the position of upper frame assembly 60 relative to base frame 54 such as the height of upper frame assembly 60 and/or amount of tilt of upper frame assembly 60 relative to base frame 54.

Beds 20a, 20b also include siderail position sensors 130 to sense the position (e.g., raised and/or lowered) of each of siderails 26, 76 and one or more caster braking sensors 60 to sense whether casters 49 are braked or released as noted above. In some embodiments, sensors 60, 130 include limit switches that are engaged or disengaged by a linkage mechanism, such as linkage 80 in the case of siderails 26, 76, to produce output signals indicative of the position of the respective mechanical structure. Alternatively, Hall effect sensors may be used as some or all of sensors 60, 130 in some embodiments. The foregoing types of sensors 60, 130 are just a couple examples of suitable sensors and therefore, this disclosure is intended to cover all types of sensors that may be used as sensors 60, 130. Each of the sensors mentioned above, including sensors internal to motors 100, 114 and sensors 60, 128, 130 are each coupled electrically to control circuitry 110 for analysis and/or processing. Thus, data from these sensors is used by the bed operating software in connection with the control and operation of various features of bed 20a, 20b and is among the features of bed 20a, 20b for which bed status data is transmitted wirelessly from module 90 to one or more WAP's 30a-30n.

As shown in FIG. 1, bed 20a, 20b includes four status or alert lights 132 at foot end 68 corresponding to various monitored features of the respective bed 20a, 20b (reference number 132 is shown in connection with only bed 20b in FIG. 1 due to space constraints). In the illustrative embodiment, for example, the four alert lights 132 of bed 20a, 20b includes a siderail position light, a bed exit/PPM disabled light, a bed exit/PPM enabled light, and a bed lowest position light. PPM is an acronym for "patient position monitoring." Alert lights 132 are coupled to a laterally extending frame member 82 of extension 99 of foot section 98 and are situated beneath footboard 72. In other embodiments, alert lights 130 may be located elsewhere on bed 20a, 20b such as on base frame 54 and/or one or more of siderails 26, 76. In FIG. 2, the four alert lights 132 are represented diagrammatically as a single block and are coupled electrically to control circuitry 110 to control the manner in which the alert lights 132 are illuminated as will be discussed in further detail below. In some embodiments, other alert lights 134, shown diagrammatically as a single block in FIG. 2, are located elsewhere on bed 20a, 20b, such as on siderails 26, 76, and are illuminated to convey information regarding other features of bed 20a, 20b, such as to indicate motor lockout conditions, alarm volume control levels, nurse call status, caster brake status, and the like.

In some embodiments, alert lights 132 are illuminated different colors to indicate certain statuses. For example, lights 132 are illuminated a first color, such as green for example, if the associated bed condition is in an acceptable or satisfactory state. Lights 132 are illuminated a second color, such as amber or yellow for example, if the associated bed condition is an undesirable or unsatisfactory state. Each of the four alert lights 132 has an icon on the lens of the respective light 132 corresponding to the monitored condition of bed 20a, 20b.

In the illustrative example, if the respective bed 20a, 20b has a falls risk protocol enabled (i.e., turned on) in which all of siderails 26, 76 are required to be raised (or a subset of siderails 26, 76 selected on GUI 24 is required to be raised), a first of the alert lights 132 is illuminated green if all of the siderails 26, 76 (or selected subset of siderails 58, 60) are in the respective raised positions (e.g., the desirable or satisfactory condition) and the first alert light 132 is illuminated amber, and in some embodiments flashed, if any one or more of siderails 26, 76 (or selected subset of siderails 26, 76) is in the lowered position (e.g., the undesirable or unsatisfactory condition). In some embodiments, a lighted iconic image corresponding to the state of the first alert light 132 is projected onto the floor at the foot end of the bed 20a, 20b. The project image has the same color and icon as the first alert light 132. If the falls risk protocol of the respective bed 20a, 20b is disabled (i.e., turned off), then the first alert light 132 is turned off and no image is projected onto the floor by bed 20a, 20b.

If the bed exit/PPM system 86 of the respective bed 20a, 20b is disabled (i.e., turned off), then a second alert light 132 is illuminated blue and a corresponding blue lighted iconic image is projected onto the floor by bed 20a, 20b in some embodiments. If the bed exit/PPM system 86 of the respective bed 20a, 20b is enabled (i.e., turned on), then the third alert light 132 is illuminated and a corresponding lighted iconic image (not shown) is projected onto the floor by bed 20a, 20b. When the third alert light 132 is illuminated, the second alert light 132 is turned off and the image associated with the second alert light 132 is no longer projected onto the floor. The third alert light 132 and associated image are illuminated green when the bed exit/PPM system 86 is armed (aka enabled) and the patient is on the bed in the proper location (e.g., the desirable or satisfactory condition). Some embodiments of each bed 20a, 20b have multiple modes (e.g., patient movement, pre-exit, and exiting modes) of system 86 with varying levels of sensitivities at which an alarm condition is considered to exist. The third alert light 132 and associated image are illuminated amber, and in some embodiments are flashed, if the bed exit/PPM system 86 is armed and the patient is not properly positioned on bed, including being out of bed altogether (e.g., the undesirable or unsatisfactory condition).

If bed 12 has the falls risk protocol enabled (i.e., turned on) control circuitry 110 monitors the position of the upper frame assembly 60 relative to base frame 54 to assure that upper frame assembly 60 is in its lowest position relative to base frame 54. If upper frame assembly 60 is in its lowest position (e.g., the desirable or satisfactory condition), the fourth alert light 132 is illuminated green (e.g., the desirable or satisfactory condition). On the other hand, if upper frame assembly 60 is not in its lowest position (e.g., the undesirable or unsatisfactory condition), the fourth alert light 132 is illuminated amber, and in some embodiments flashed. In some embodiments, a lighted iconic image corresponding to the state of the fourth alert light 132 is projected onto the floor at the foot end 68 of the respective bed 20a, 20b. The image associated with the fourth alert light 132 has the same color and icon as the fourth alert light 132. If the falls risk protocol of the respective bed 20a, 20b is disabled (i.e., turned off), then the fourth alert light 132 is turned off and no associated image is projected onto the floor.

In some embodiments, an audible alarm of each bed 20a, 20b may also sound under the control of control circuitry 110 if an unsatisfactory condition of a particular protocol or condition is detected for the particular bed 20a, 20b. Alert lights 132 are illuminated a third color if the associated protocol or condition is enabled for monitoring and at least one of the monitored bed statuses for the particular protocol or condition is undesirable (i.e., violated), but the associated alert has been suspended by the caregiver. If the alert has been suspended, any associated audible alarms may be turned off during the alarm suspension. A caregiver may suspend an alert associated with alert lights 132, for example, when assisting a patient in getting out of the respective bed 20a, 20b and going to the bathroom. The various alert conditions (aka alarm conditions) associated with the operation of alert lights 132 and the audible alarms, if any, of each bed 20a, 20b is among the features of bed 20a, 20b for which bed status data is transmitted wirelessly from module 90 to one or more WAP's 30a-30n.

In some embodiments, bed 20a or bed 20b optionally includes a wired communication module 136 that is electrically coupled to control circuitry 110 as shown diagrammatically in FIG. 2 (in dotted line). A datalink 138 couples the wired communication module 136 with a location unit 140 that is mounted at a fixed location in the respective room, such as room 12, as shown in FIG. 1 (in dotted line). In particular, location unit 140 is mounted to a room wall in FIG. 1 but may just as well be mounted to headwall unit 40 or some other fixed architectural product (e.g., bed locator unit or service chase) in the room. Datalink 138 comprises a wired datalink, such as a nurse call cable or Ethernet cable, in some embodiments such as the embodiment illustrated in FIG. 1. One example of a nurse call cable is a 37-pin nurse call cable available from Hill-Rom Company, Inc. of Batesville, Indiana. In variant embodiments, module 136 communicates with location unit 140 wirelessly and therefore, datalink 138 comprises a wireless datalink, such as an infrared, ultrasonic, or Bluetooth Low Energy (BLE) connection, between module 136 and location unit 140.

In the description of the use of location unit 140 in system 10 that follows, it will be assumed that bed 20a is the bed connected to location unit 140 by datalink 138. In some embodiments, location unit 140 sends a location ID to bed 20a and then bed 20a, in turn, transmits the location ID along with the bed ID and bed status data as the WiFi messages from wireless communication module 90 for receipt by WAP's 30a-30n for subsequent transmission to one or more of servers 34, 36, 38 along with the signal strength data. The location ID from location unit 140 correlates to the particular room, such as room 12, in which the location unit 140 is mounted. Thus, if bed 20a is equipped with wired communication module 136 that receives the location ID from location unit 140, it is not necessary for bed 20a to be equipped with the manual location ID entry capability discussed above.

In some embodiments, location unit 140 is a standalone unit that is not connected to network 32 other than through datalink 138, bed 20a, and one or more of WAP's 30a-30n. In such embodiments, the data flow of the location ID is from location unit 140 to bed 20a, then to one or more WAP's 30a-30n from wireless communication module 90 of bed 20a, then to one or more of servers 34, 36, 38 from the one or more WAP's 30a-30n via the network 32. In FIG. 2, network 32 is labeled as "communication infrastructure/Ethernet." In other embodiments, location unit 140 is coupled to network 32 directly as indicated diagrammatically in FIG. 2 by datalink 142 (in dotted line). In some such embodiments, the bed ID of bed 20a is transmitted to location unit 140 from module 136 and then the bed ID and location ID are transmitted to one or more of servers 34, 36, 38 via datalink 142 and network 32. The bed ID and location ID are then used by the locating server 38 to correlate bed 20a with its location.

In the embodiments in which the bed ID is sent to location unit 140 and then the location ID and bed ID are sent via datalink 142 and network 32 to one or more of servers 34, 36, 38, other data such as some or all of the bed status data is still transmitted from wireless communication module 90 to one or more of WAP's 30a-30n. Thus, a signal strength profile is still able to be built for bed 20 located in room 12 by one or more of servers 34, 36, 38 based on the WiFi messages sent by bed 20a from module 90. For example, it is within the scope of the present disclosure for high priority alerts from bed 20a, such as nurse call alerts generated by the patient pressing a nurse call button on control panel 122 of bed 20a, bed exit alerts generated by the scale/PPM system 86, or other alerts indicating that the falls risk protocol of bed 20a is being violated, to be sent from module 136 of bed 20a via location unit 140 and then via datalink 142 and network 32 to nurse call server 34. However, other bed status data and alerts that are not high priority alerts, sometimes referred to as normal priority alerts, may be transmitted wirelessly from module 90 of bed 20a to WAP's 30a-30n and then on to one or more of servers 34, 36, 38 via network 32.

In some embodiments, the location unit 140 comprises an audio station bed connector (ASBC), a bed interface unit (BIU), a network interface unit (NIU), a wireless interface unit (WIU), or a Universal Collector (UC) of the type available from Hill-Rom Company, Inc. of Batesville, Indiana. The ASBC ID or BIU ID or NIU ID or WIU ID or UC ID, as the case may be, or the media access control (MAC)

addresses of these devices, or the Internet Protocol (IP) addresses of these devices, may serve as the location ID that correlates to the room in which these devices are located at the option of the system designer. Alternatively, a custom location ID may be stored in memory of the microprocessor-based circuitry of the these devices for transmission to network 32 via a port, such an input/output port of these devices. Further details of BIU's and NIU's are shown and described in U.S. Pat. Nos. 7,538,659 and 7,319,386 and in U.S. Patent Application Publication Nos. 2009/0217080 A1, 2009/0212925 A1 and 2009/0212926 A1, each of which are hereby expressly incorporated by reference herein. Further details of WIU's are shown and described in U.S. Patent Application Publication No. 2007/0210917 A1 which is hereby expressly incorporated by reference herein. Further details of UC's are shown and described in connection with FIGS. 11A-18 of U.S. Patent Application Publication No. 2017/0323555 A1 which is hereby incorporated herein by reference herein.

Figure 3A:
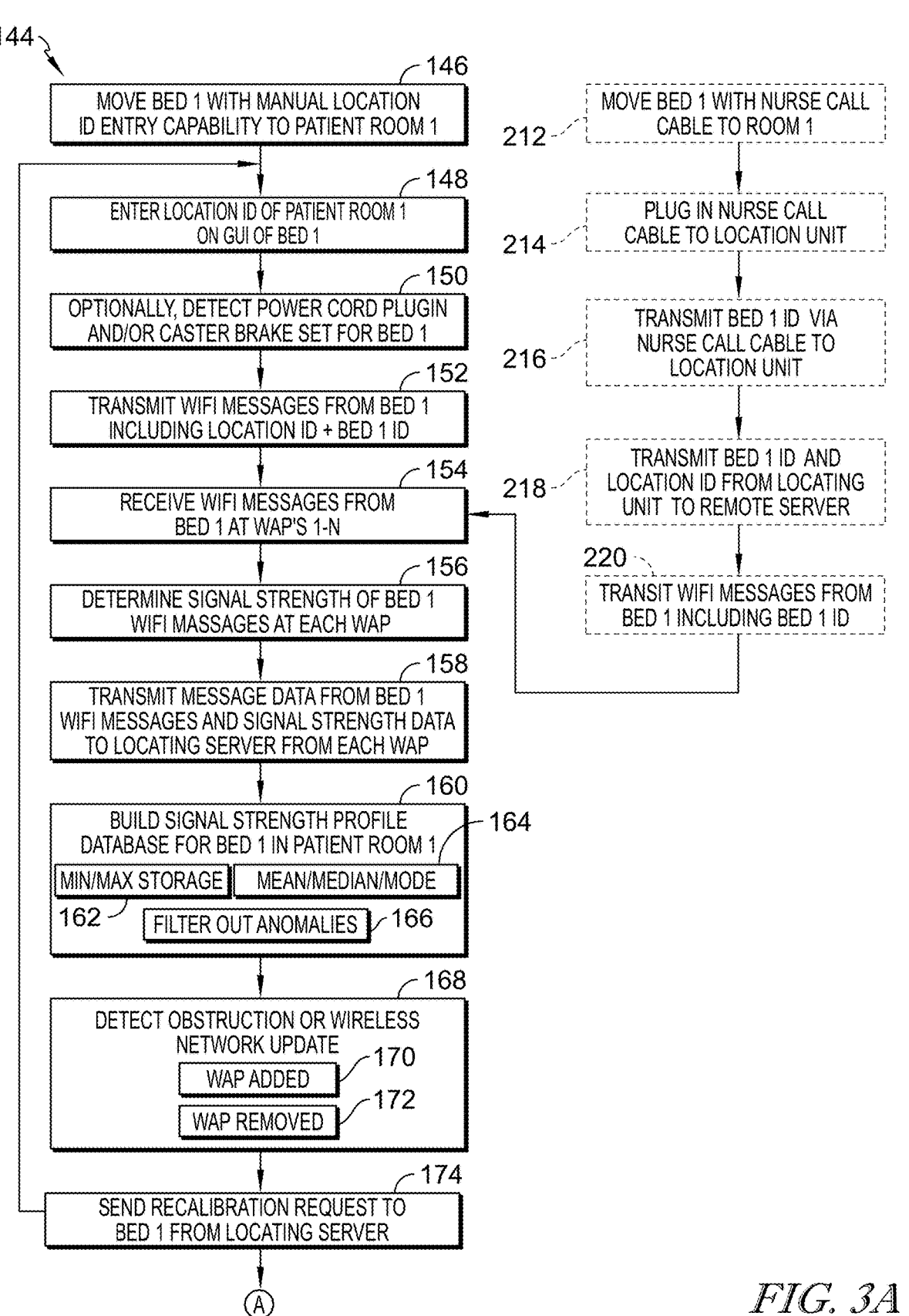

Referring now to FIGS. 3A-3C, a method 144 implemented within system 10 is disclosed. Some portions of method 144 are performed by caregivers and other portions of method 144 are performed by computer devices of one or more of systems 35, 39, and 41, such as by servers 34, 36, 38. Still further portions of method 144 are performed by one or more of WAP's 30a-30n. In the description that follows, it will be assumed that locating server 38 is performing certain portions of method 144 but it should be understood that some or all of these portions of method 144 may be performed by servers 34, 36 or other computer devices of system 10 as desired. Thus, the software functionality of method 144 may be distributed among multiple computer devices in some embodiments.

As shown in FIG. 3A, method 144 begins when a first bed (designated as "BED 1" in FIGS. 3A-3C), such as bed 20a, having manual location ID entry capability is moved into a first patient room (designated as "PATIENT ROOM 1" in FIGS. 3A-3c), such as room 12, as indicated at block 146. In FIG. 1, room 12 is labeled arbitrarily as ROOM 2 but that is considered to be the first patient room in the illustrative example. After the first bed 20a has been moved to the first patient room 12, a caregiver enters the location ID of the first patient room 12 on GUI 24 of bed 20a as indicated at block 148. As indicated at block 150, method 144 optionally includes detecting that power cord 48 of bed 20a is plugged into a power receptacle, such as receptacle 50, and/or that the caster brakes of one or more of casters 56 of bed 20a are set such that the one or more casters 56 of bed 20a are braked.

From block 150, or from block 148 if optional block 150 is omitted, method 144 proceeds to block 152 at which WiFi messages are transmitted from the first bed 20a. The transmitted WiFi messages include the location ID and the bed ID of the first patient bed 20a as also indicated at block 152. The transmitted WiFi messages from the first patient bed 20a are received at one or more of WAP's 30a-30n (designated as "WAP's 1-N" in FIGS. 3A-3C) as indicated at block 154. In block 154, it is assumed that all of WAP's 1-N receive the WiFi messages from bed 20a, but only a subset of WAP's 1-N may receive the WiFi messages in some instances or embodiments.

From block 154, method 144 proceeds to block 156 at which signal strength of the WiFi messages received from the first patient bed 20a at each of the receiving WAP's 1-N is determined by the respective receiving WAP 1-N. After the signal strength of the WiFi messages from the first patient bed 20a are determined at the receiving WAP's 1-N, the respective WAP's 1-N, or subset thereof as the case may be, transmit the message data contained in the WiFi messages from the first patient bed 20a along with the determined signal strength data to locating server 38 as indicated at block 158.

After receiving the transmissions from WAP's 1-N that contain the signal strength data of the WiFi messages from the first patient bed 20a, locating server 38 builds a signal strength profile database (sometimes referred to herein as simply a "signal strength profile") for the first patient bed 20a in the first patient room 12 as indicated at block 160 of FIG. 3A. In connection with building the bed 1/room 1 signal strength profile, locating sever 38 accumulates signal strength values as data points over time on a WAP-by-WAP basis for multiple transmissions of WiFi messages from the first patient bed 20a. The accumulated signal strength data points are then used by locating server 38 to determine and store on a WAP-by-WAP basis a minimum signal strength value and a maximum signal strength value for the bed 1/room 1 WiFi messages as indicated by sub-block 162 of block 160.

As indicated at sub-block 164 of block 160, locating server 38 also determines on a WAP-by-WAP basis, a mean (aka average) signal strength value, a median signal strength value, and a mode signal strength value for the bed 1/room 1 WiFi messages. The mean signal strength value is the sum of the accumulated signal strength data points divided by the number of signal strength data points. The median signal strength value is the "middle" value of the accumulated signal strength data points. The mode signal strength value is the signal strength value that appears most often in the accumulated signal strength data points. As noted above, the signal strength profile may be built based on WiFi messages received from bed 20a during a preset amount of time (e.g., 5 minutes, 10 minutes, 2 hours, 4 hours, 8 hours, etc.) or based on the WiFi messages received from bed 20a for the entirety of the time that bed 20a is located in room 12 and is generally stationary.

With regard to accumulating the signal strength values for each of the WAP's 1-N in some embodiments, locating server 38 filters out any anomalies in the signal strength data points as indicated at sub-block 166 of block 168. Anomalies may include, for example, "flyer" data points that are significantly higher or significantly lower than the typical values of the signal strength data points being accumulated, such as being 30% higher or lower, 40% higher or lower, 50% higher or lower, etc. than, say, a rolling average of the data points as they accumulate. For example, if the rolling average signal strength value of a given WAP for the bed 1/room 1 Wifi messages is −40 decibels (dB), then signal strength values of −52 dB or greater in absolute value (e.g., 30% of −40 dB is −12 dB) or −28 dB or lower in absolute value, then such signal strength values are ignored and/or not accumulated.

The level at which signal strength values or data points are filtered out as anomalies are at the discretion of the system designer and so the % values given above are intended to represent just a few arbitrary examples. A set signal strength deviation threshold, such as +/−10 dB, +/−15 dB, +/−20 dB, etc. may be used instead of a % for determining whether particular signal strength data points are considered to be anomalies as compared to the baseline or accumulated average, if desired. Alternatively or additionally, the anomalous signal strength data that is filtered out may include signal strength data below a predetermined signal strength threshold such as below −80 dB or −90 dB, for example.

After building the signal strength profile for bed 1/room 1 at block 160 of FIG. 3A, method 144 proceeds to block 168 at which locating server 38 determines whether any major changes have occurred within the system 10 that would have a tendency to dramatically change the signal strength profile for bed 1/room 1. As indicated in block 168, the detection of a major change in system 10 may be the result of an obstruction being introduced within room 12 between bed 20a and the WAP's 30a-30n that receive the WiFi messages from bed 20a. For example, imaging equipment (e.g., fluoroscopy equipment, magnetic resonance imaging (MRI) equipment, X-ray equipment, or the like) may be transported to room 12 and located so as to interfere with the WiFi signals transmitted from bed 20a thereby abruptly changing the signal strength data points being received from multiple WAP's. On the other hand, the abrupt change may be the result of movement of bed 20a within the associated room or out of the associated room.

As also indicated in block 168, the detection of a major change in system 10 may result from another WAP being added to those that are receiving WiFi messages from bed 20a, as indicated at sub-block 170 of block 168. The additional WAP may simply be one that has been added into system 10 and connected to network 32 such that signal strength data is still received from all of the WAP's from which such signal strength data was previously received, plus receiving the signal strength data from the new WAP. On the other hand, receiving transmissions from the new WAP at locating server 38 may be indicative that bed 20a is being moved.

Still further, the detection of a major change in system 10 may result from another WAP being removed from those that are receiving WiFi messages from bed 20a, as indicated at sub-block 172 of block 168. The removed WAP may simply be one that has been disconnected from network 32 such that signal strength data is still received from all of the other WAP's from which such signal strength data was previously received, but the signal strength data from the removed WAP is no longer received. On the other hand, the absence of transmissions, including signal strength data, from the removed WAP at locating server 38 may be indicative that bed 20a is being moved.

In response to detection of a major change in system 10 by locating server 38 at block 168, a recalibration request is sent to the first patient bed 20a from locating server 38 as indicated at block 174 of FIG. 3A. If the first patient bed 20a receives such a recalibration request, method 144 returns back to block 148 so that a caregiver can enter (or re-enter, if appropriate) the location ID of the patient room on GUI 24 of the first patient bed 20a and then, method 144 proceeds from block 148 as described above. In some embodiments, if a recalibration request is made by server 38 at block 174, the signal strength profile data points accumulated prior to the recalibration request are deleted or ignored and a new signal strength profile for bed 1/room 1 begins to be built or created by locating server 38.

If no major change in system 10 is detected at block 168 of FIG. 3A, then the recalibration request of block 174 is skipped and method 144 proceeds to block 176 of FIG. 3B. At block 176, locating server 38 detects the removal of the first patient bed 20a from room 12 which is considered to be the first patient room in the illustrative example even though labeled as "ROOM 2" in FIG. 1. The present disclosure contemplates different ways that locating server 38 detects removal of bed 20a from room 12, or at least preparation for removal of bed 20a from room 12. For example, loss of WiFi messages from bed 20a as indicated at sub-block 178 of block 176, is indicative that the WiFi communication capability of bed 20a has been turned off in preparation of transport of bed 20a to a new location. In any event, it is not possible for locating server 38 to continue to build the signal strength profile for bed 1/room 1 if signal strength data points are no longer being received due to a loss of WiFi messages from bed 20a.

As indicated at sub-block 180 of block 176, unplugging of power cord 48 of bed 20a from receptacle 50 is another way in which locating server 38 determines that bed 20a is getting ready to be moved from room 12 to a new location. As noted previously, the bed status data transmitted from bed 20a includes information indicating whether or not bed 20a is receiving AC power via power cord 48. As indicated at sub-block 182 of block 176, unbraking or releasing of casters 56 of bed 20a is yet another way in which locating server 38 determines that bed 20a is getting ready to be moved from room 12 to a new location.

After the first patient bed 20a is removed from the first patient room 12, the second patient bed 20b is moved into the first patient room 12 as indicated at block 184 of FIG. 3B. As indicated in block 184, in the illustrative example, bed 20a does not have manual location ID entry capability and does not have any cable 138, such a nurse call cable, that interconnects bed 20b with location unit 140. As indicated at block 186, method 144 optionally includes detecting that a power cord of bed 20b (not shown, but substantially the same as power cord 48 of bed 20a) is plugged into a power receptacle, such as receptacle 50, and/or that the caster brakes of one or more of casters 56 of bed 20b are set such that the one or more casters 56 of bed 20b are braked.

From block 186, or from block 184 if optional block 186 is omitted, method 144 proceeds to block 188 at which WiFi messages are transmitted from the second patient bed 20b. The transmitted WiFi messages transmitted for bed 20a includes the bed ID of bed 20b but do not include any location ID. The transmitted WiFi messages from the second patient bed 20b are received at one or more of WAP's 30a-30n (designated as "WAP's 1-N" in FIGS. 3A-3C) as indicated at block 190. In block 190, it is assumed that all of WAP's 1-N receive the WiFi messages from bed 20b, but only a subset of WAP's 1-N may receive the WiFi messages from bed 20b in some instances or embodiments.

From block 190, method 144 proceeds to block 192 at which signal strength of the WiFi messages received from the second patient bed 20b at each of the receiving WAP's 1-N is determined by the respective receiving WAP 1-N. After the signal strength of the WiFi messages from the second patient bed 20b are determined at the receiving WAP's 1-N, the respective WAP's 1-N, or subset thereof as the case may be, transmit the message data contained in the WiFi messages from the second patient bed 20b along with the determined signal strength data to locating server 38 as indicated at block 194.

After receiving the transmissions from WAP's 1-N that contain the signal strength data of the WiFi messages from the second patient bed 20b, locating server 38 builds a signal strength profile database (aka a "signal strength profile") for the second patient bed 20b as indicated at block 196 of FIG. 3B. In connection with building the bed 2 signal strength profile, locating sever 38 accumulates signal strength values as data points over time on a WAP-by-WAP basis for multiple transmissions of WiFi messages from the second patient bed 20b. The accumulated signal strength data points are then used by locating server 38 to determine and store on a WAP-by-WAP basis a minimum signal strength value and a maximum signal strength value for the bed 2 WiFi messages as indicated by sub-block 198 of block 196.

As indicated at sub-block 200 of block 196, locating server 38 also determines on a WAP-by-WAP basis, a mean (aka average) signal strength value, a median signal strength value, and a mode signal strength value for the bed 2 WiFi messages. The mean signal strength value, the median signal strength value, and the mode signal strength value for the bed 2 WiFi messages of sub-block 200 are determined in the same manner as described above in connection with sub-block 164 of block 160 pertaining to the bed 1/room 1 WiFi messages and so the description is not repeated.

With regard to accumulating the signal strength values for each of the WAP's 1-N in some embodiments, locating server 38 filters out any anomalies in the signal strength data points pertaining to the WiFi messages from the second patient bed 20b as indicated at sub-block 202 of block 196. The discussion above of sub-block 166 and the anomalies that may occur in connection with the WiFi messages from the first patient bed 20a is equally applicable to sub-block 202 and the anomalies that may occur in connection with the WiFi messages from the second patient bed 20b and so the description is not repeated.

After the signal strength profile for bed 2 (aka the second patient bed 20b) is built by locating server 38 at block 196, method 144 proceeds to block 204 at which the locating server 38 compares the signal strength profile for bed 2 to the signal strength profile of bed 1 and to all of the other signal strength profiles stored in a database of the locating server 38 or in some other database of a data storage device of system 10. At block 206 of method 144, locating server 38 detects a match between the bed 2 signal strength profile and the bed 1 signal strength profile which is the expected result since bed 20b is located in room 12 at the same place at which bed 20a was located when the bed 1 signal strength profile was created. In fact, it is envisioned that bed 20b will be positioned in room 12 relative to headwall 40 at substantially the same spot that bed 20a was positioned when it occupied room 12.

As indicated at sub-block 208 of block 206, the present disclosure contemplates that detecting a match between the signal strength profiles of the first patient bed 20a and the second patient bed 20b, involves comparing one or more of the median, mean, and mode values of the signal strength profile of bed 20b for each WAP 1-N with the minimum and maximum signal strength values of the signal strength profile of bed 20a for each WAP 1-N. Thus, just one of the mean, median, and mode values of the bed 2 signal strength profile for each WAP is compared to the minimum and maximum signal strength values of the bed 1 signal profile for the respective WAP in some embodiments of method 144 of system 10. In other embodiments, two of the mean, median, and mode values of the bed 2 signal strength profile for each WAP are compared to the minimum and maximum signal strength values of the bed 1 signal profile for the respective WAP. In still other embodiments, all three of the mean, median, and mode values of the bed 2 signal strength profile for each WAP are compared to the minimum and maximum signal strength values of the bed 1 signal profile for the respective WAP. For each of the mean, median, and mode values, as the case may be, of the signal strength profile of bed 2 that are numerically between the minimum and maximum values of the signal strength profile of bed 1, a match is considered to exist between bed 2 and bed 1 with regard to the respective WAP.

In some embodiments, detecting a match between the signal strength profiles of the first patient bed 20a and the second patient bed 20b, involves determining that one, two, or three of the mean, median, and mode values for the second patient bed 20b are within a threshold tolerance range of the respective one, two, or three values of the mean, median, and mode, as the case may be, for the first patient bed 20a. The tolerance range may be plus or minus some predetermined signal strength value such as +/−5 dB, +/−7.5 dB, or +/−10 dB, just to give a few arbitrary examples. Alternatively, the tolerance range may be plus or minus some predetermined percentage of the respective bed 1 mean, median, and mode signal strength values such as 5%, 6.8%, or 10%, just to give a few arbitrary examples. In some embodiments, a comparison between minimum and maximum signal strength values of the second patient bed 20b being within a tolerance range of the minimum and maximum signal strength values of the first patient bed 20a to determine a match for a given WAP may be made by locating server 38 in addition to or in lieu the methodologies for determining a match described above.

In order to determine a match between the overall signal strength profile of bed 2 with some other previously stored signal strength profile, locating server 38 determines which of the signal strength profile comparisons yields the most WAP signal strength matches regardless of the methodology used to determine the match. After locating server 38 detects the match between the signal strength profile of bed 2 with that of bed 1, method 144 advances to block 210 at which the locating server 38 associates bed 2 (aka the second patient bed 20b) with room 1 (aka room 12 which is labeled as ROOM 2 in the illustrative example). Once the association between the second patient bed 20b and room 12 is made by locating server 38, method 144 terminates with regard to determining the location of the second patient bed 20b.

As noted previously, in alternative embodiments of system 10, bed 20a does not have manual location ID entry capability but instead, couples to location unit 140 with communication cable 138 and location unit 140 is, in turn, coupled to network 32 by communication link 142. In some embodiments, communication link 142 comprises dedicated cabling, such as CAT-5 cabling or CAT-5e Ethernet cabling, which connects location unit 140 to nurse call server 34 or some other component of nurse call system 35 without involving any other equipment of network 32. In such alternative embodiments in which bed 20a communicates with location unit 140, method 144 is altered slightly as discussed below.

Referring once again to FIG. 3A, the alternative method 144 pertaining to bed 20a without manual location ID entry capability starts by moving bed 1 (aka the first patient bed 20a) with nurse call cable 138 to room 1 (aka the first patient room 12, labeled as ROOM 2 in FIG. 1) as indicated at dotted block 212. Once located in room 12, the nurse call cable 138 is plugged into the location unit 140 as indicated at dotted block 214. If not already plugged into the nurse call port of bed 20a, an opposite end of cable 138 has its connector, such as 37-pin connector, plugged into the nurse call port of bed 20a. After the nurse call cable 138 is plugged in so as to interconnect bed 20a with location unit 140, the bed ID of bed 20a is transmitted to location unit 140 as indicated at dotted block 216. In some embodiments, other bed status data such as high priority alerts is communicated from bed 20a to location unit 140 via cable 138.

It should be noted that interconnecting bed 20a and location unit 140 using cable 138 assures that bed 20a is intended to remain relatively stationary in room 12. Thus, there is no need to detect whether or not the power cord 48 is plugged into an AC power outlet. However, if desired, such optional detection of the power cord 48 also being plugged in can be implemented in the alternative method 144. The same goes for detecting that the casters 56 of bed 20*a* are braked. However, in the illustrative example of the alternative method 144 shown in FIG. 3A, the optional detection of power cord plug in and/or caster brake setting is omitted.

After the bed ID of bed 20*a* is transmitted to the location unit 140 at dotted block 216, the location unit 140 transmits the bed ID and location ID to the locating server 38 as indicated at dotted block 218. In the illustrative example, the transmission of the bed ID and location ID to locating server 38 from location unit 140 is done via data link 142 and, in some embodiments, network 32. At dotted block 220, the first patient bed 20*a* transmits WiFi messages to one or more of WAP's 30*a*-30*n* and such WiFi messages include the bed ID. The alternative method then advances from dotted block 220 to block 154 and proceeds from there in the same manner as described above.

The WiFi messages transmitted by bed 20*a* at block 220 includes bed status data along with the bed ID. The data in the WiFi messages, including the bed ID, is transmitted from the receiving WAP's 30*a*-30*n* to one or more of servers 34, 36, 38. By using the bed ID, the one or more servers 34, 36, 38 are then able to cross-correlate the bed status data with the location ID for room 12 that has been transmitted via location unit 140. The locating server 38 is also able to cross-correlate the signal strength values of the WiFi messages from bed 20*a* to room 12 by using the bed ID which is common to the WiFi messages from bed 20*a* and the transmissions from bed 20 via location unit 140.

In a variant embodiment of method 144, datalink 142 is omitted and location unit 140 is a standalone unit that transmits the location ID to bed 20*a* via cable 138 or via one of the alternative datalinks 138 described above (e.g., infra-red, ultrasound, BLE, etc.). In such a variant method, dotted blocks 212, 214 remain as shown in FIG. 3A. However, dotted block 216 is altered to state "TRANSMIT LOCA-TION ID VIA NURSE CALL CABLE TO BED 1" in the variant embodiment. Also, in the variant embodiment, dot-ted blocks 218, 220 are omitted and the variant embodiment of method 144 proceeds from the altered dotted block 216 to block 152 and proceeds from there in the same manner as described above.

While method 144 was described above with regard to bed 20*a* being replaced by bed 20*b* in room 12 and the manner in which the signal strength profile of bed 20*b* is compared to the signal strength profile of bed 20*a* created while bed 20*a* was in room 12, it should be appreciated that locating server 38 implements method 144 for a multitude of beds in a multitude of rooms (e.g., ROOMS 1-M) of the healthcare facility. According to this disclosure therefore, it is theoretically possible for a healthcare facility to have just one bed, like bed 20*a*, that is equipped with manual location ID entry capability, or nurse call cable connectivity capa-bility, and to transport that one bed from room-to-room so that locating server 38 can build the signal strength profile for each room to which the signal strength profiles of other beds not having manual location ID entry capability, or not having nurse call cable connectivity capability, are com-pared.

Referring now to FIG. 4, a table 222 of data correspond-ing to the first signal strength profile for the first patient bed 20*a* when located in the first patient room 12 is shown generically. In the first column, the WAP number or name is shown. Beneath each WAP name the text "(FREQUENCY 1)," "(FREQUENCY 2)," "(FREQUENCY 3)," etc. This indicates that each WAP is assigned its own communication channel at a discrete, unique frequency as compared to those assigned to the other WAP's. The other columns of table 222 are labeled MIN, MAX, MEAN, MEDIAN, and MODE and the data within these columns has been described herein already. The minimum and maximum signal strengths are indicated in the format "$SS_{MIN\ WAP\ \#-BED\ \#}$" and "$SS_{MAX\ WAP\ \#-BED\ \#}$" in table 222. The same "WAP #-BED #" format is used for the MEAN, MEDIAN, and MODE data as well. So, for example, $SS_{MAX\ 3-1}$ is the maximum signal strength value of the WiFi messages received at WAP 3 from bed 1 while bed 1 is located in room 1. Similarly, MEDIAN 2-1 is the determined median signal strength value of the WiFi messages received at WAP 2 from bed 1 while bed 1 is located in room 1.

Referring now to FIG. 5, a table 224 of data correspond-ing to a second signal strength profile for the second patient bed 20*b* when located in the first patient room, but initially, server has not determined the location of bed 20*b*. The data at each block of table 224 having data is compared to the data of the corresponding block of table 222 having data in any of the manners described above to determine a match between the analyzed data of table 224 with that of table 222. Thus, tables 222, 224 are provided herein to facilitate an understand of block 206 of method 144. It is contem-plated by the present disclosure that each block of table 224 that meets the matching criteria with the corresponding block of table 222 can be designated with some sort of positive match indicator (e.g., "Y" or "match" or "+" just to give a few examples) and each block of table 224 that does not meet the matching criteria with the corresponding block of table 222 can be designated with some sort of negative match indicator (e.g., "N" or "no match" or "−" just to give a few examples).

While determining the room in which the second patient bed 20*b* is located, locating server 38 compares the data from table 224 to a multitude of signal strength profiles similar to table 222 and corresponding to each of ROOMS 1-M. Whichever comparison yields the greatest number of positive match indicators is determined by locating server 38 to be the room in which the second patient bed 20*b* is located. In some embodiments, if there is a tie between the number of positive match indicators in connection with two or more of rooms 1-M, then the match criteria is tightened, such as by changing the tolerance range for determining a match from +/−10 dB to +/−5 dB, or from 10% to 4%, just to give a couple arbitrary example, and the matching analy-sis between the tying rooms is re-run by locating server 38. Multiple iterations of tightening the matching criteria might be needed before the ties in the number of positive match indicators are eliminated.

Figure 6:
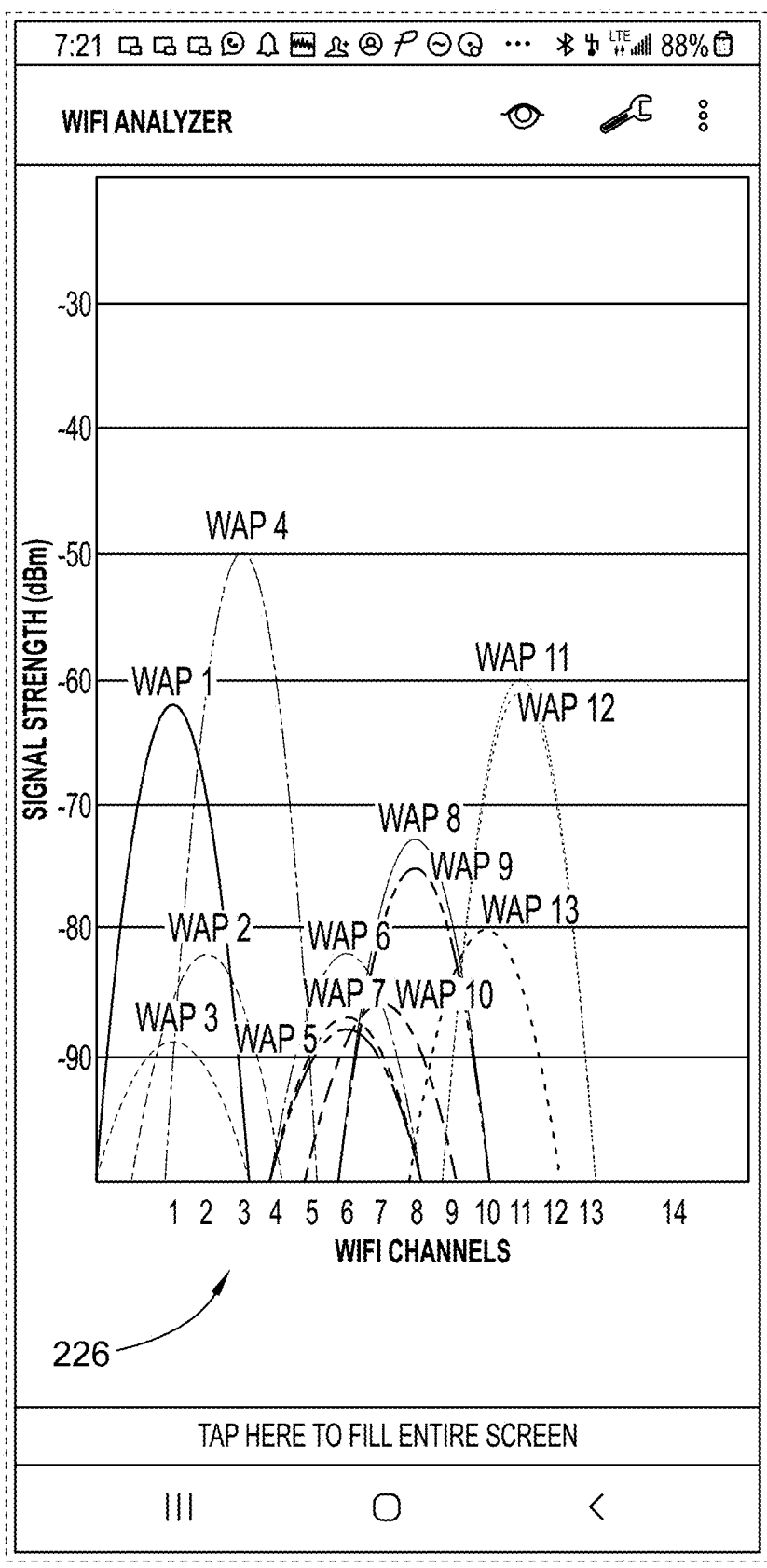
FIG. 6 is a graph generated by a WiFi analyzer when the first patient bed is in the first patient room.

Referring now to FIG. 6, a graph 226 generated by a WiFi analyzer is shown and corresponds to the first patient bed 20*a* being located in the first patient room 12. In the illustrative example of graph 226, there are thirteen WAP's that receive WiFi signals from bed 20*a*. The parabolas in graph 226 are labeled with the respective WAP name or number. The x-axis of graph 226 generically indicates the WiFi channel (corresponding to a designated frequency) for each of the WAP's and the y-axis indicates the signal strength in decibel-milliWatts (dBm). When dB is used herein, it is intended to be synonymous with dBm. The tips of the parabolas in graph 226 indicate the instantaneous signal strength of WiFi messages received at the respective WAP from the first patient bed 20*a*. Over time, the tips of the parabolas increase and decrease vertically in graph 226 due to environmental conditions (e.g., entry and exit of people and equipment into the room) but the parabolas remain centered on the designated frequency of the channel for the respective WAP.

Figure 7:
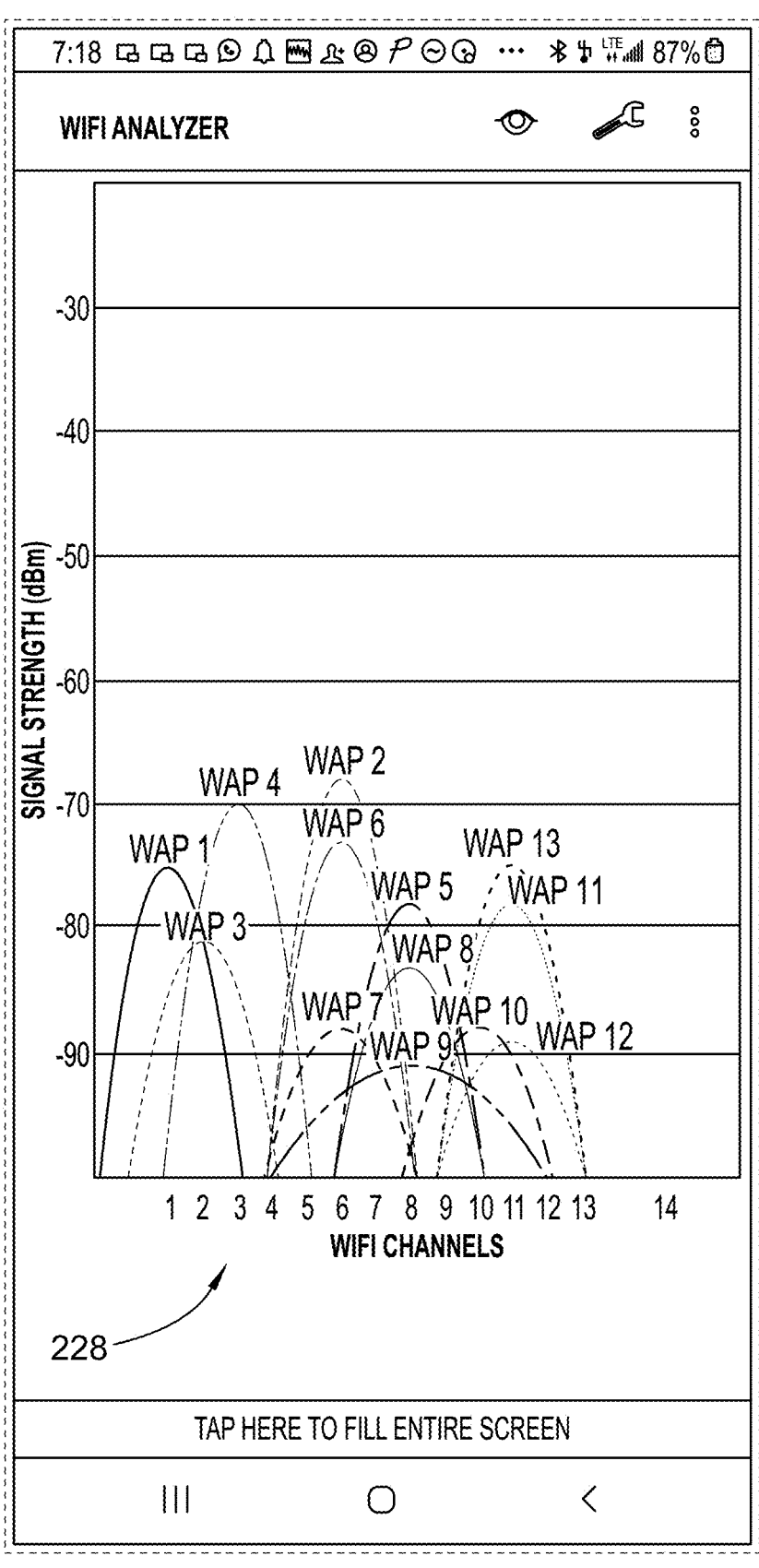
FIG. 7 is a graph generated by the WiFi analyzer when the first patient bed is in a second patient room.

Referring now to FIG. 7, a graph 228 is generated by the WiFi analyzer when the first patient bed 20a is located in a second patient room. The description above of the various aspects of graph 226 is equally applicable to graph 228 and so is not repeated. Graph 228 is provided to show an example as to how the size and shapes of the parabolas for the various WAP's change when bed 20a is moved to a new location. It should be appreciated therefore, that the numeric signal strength values populated in table 222 when bed 20a is in the first patient room (e.g., ROOM 2) will be substantially different than the signal strength values that would be populated in a similar table when bed 20a is in the second patient room (e.g., ROOM 1 or ROOM 3).

Figure 8:
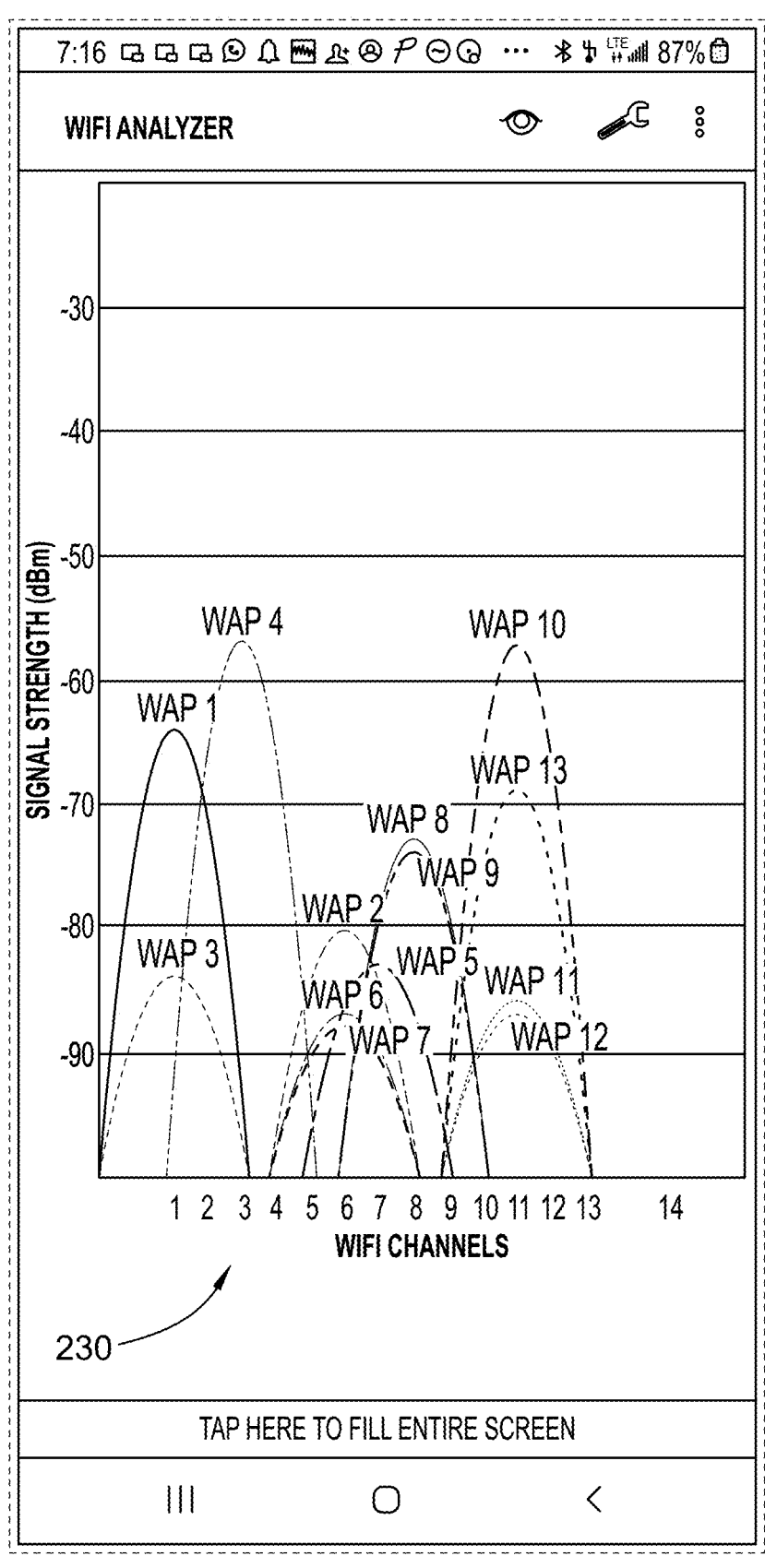
FIG. 8 is a graph generated by the WiFi analyzer when the second patient bed is in the first patient room.

Referring now to FIG. 8, a graph 230 is generated by the WiFi analyzer when the second patient bed 20b is in the first patient room 12. The description above of the various aspects of graph 226 is equally applicable to graph 230 and so is not repeated. By comparing graph 230 of FIG. 8 with graph 226 of FIG. 6, it can be seen that the parabolas for WAP 1, WAP 4, WAP 8 and WAP 9 are quite similar. Thus, numeric data of the signal strength profiles of these four WAP's for bed 20a and bed 20b when located in room 12 will also be quite similar such that when the matching methodologies described above are implemented by locating server 38, a determination will be made by locating server 38 that bed 20b is, in fact, located in room 12.

Based on the foregoing, therefore, the present disclosure contemplates that locating server 38 detects a signal strength profile match by determining that the signal strength data in the WiFi messages from the second patient bed 20b for a preset number of WAP's is between the respective minimum signal strength values and maximum signal strength value for each of the preset number of WAP's as calculated based on the WiFi messages from the first patient bed 20a. In particular, the preset number of WAP's is less than all of the WAP's in communication with the second patient bed 20b. If desired, the preset number of WAP's corresponds to a set number of WAP's having highest signal strength from among the plurality of WAP's in communication with the second patient bed 20b. For example, the set number is at least four in some embodiments.

There are a number of companies and individuals that offer WiFi analyzer software that can be used to create graphs 226, 228, 230 or graphs similar to graphs 226, 228, 230 as well as providing other data regarding WiFi connectivity in a network. The following is a partial list of suitable WiFi analyzer software: NetSpot from Etwok, Inc.; OpenSignal from Opensignal Limited; ScanFi from Vikrant Waghmode; WiFi Analyzer from Master Internet s.r.o.; Network Signal Info from KAIBITS Software GmbH; and Network Analyzer from Jiri Techet.

Although certain illustrative embodiments have been described in detail above, variations and modifications exist within the scope and spirit of this disclosure as described and as defined in the following claims.

The invention claimed is:
1. A wireless locating method comprising
entering a location identification (ID) on a user interface (UI) of a first piece of equipment having manual location ID entry capability, the location ID correlating to a building location at which the first piece of equipment is located,

transmitting from the first piece of equipment first wireless fidelity (WiFi) messages including the location ID and a first equipment ID for receipt by a plurality of wireless access points (WAP's) of a computer network of a building,
determining signal strengths of the first WiFi messages received at each of the WAP's of the plurality of WAP's,
storing the signal strengths of the first WiFi messages as a first signal strength profile in memory of a locating server, the first signal strength profile being indicative of the building location in which the first piece of equipment is located;
removing the first piece of equipment from the building location;
transporting a second piece of equipment to the building location, the second piece of equipment lacking manual location ID entry capability,
transmitting from the second piece of equipment second WiFi messages including a second equipment ID for receipt by the plurality of WAP's of the computer network of the building,
determining signal strengths of the second WiFi messages received at each of the WAP's of the plurality of WAP's,
storing the signal strengths of the second WiFi messages as a second signal strength profile in memory of the locating server,
comparing the second signal strength profile with the first signal strength profile, and
if the second signal strength profile substantially matches the first signal strength profile, determining by the locating server that the second piece of equipment is located at the building location.
2. The wireless locating method of claim 1, wherein the first WiFi messages include power plug status data indicative of whether a power plug of the first piece of equipment is plugged into a power receptacle and wherein storing the signal strengths of the first WiFi messages as the first signal strength profile occurs only if the power plug status data indicates that the power plug of the first piece of equipment is plugged into the power receptacle.
3. The wireless locating method of claim 1, wherein the second WiFi messages include power plug status data indicative of whether a power plug of the second piece of equipment is plugged into a power receptacle and wherein storing the signal strengths of the second WiFi messages as the second signal strength profile occurs only if the power plug status data indicates that the power plug of the second piece of equipment is plugged into the power receptacle.
4. The wireless locating method of claim 1, wherein storing the signal strengths of the first WiFi messages as the first signal strength profile comprises receiving the first WiFi messages over a threshold amount of time and storing in the server minimum signal strength values and maximum signal strength values for each WAP of the plurality of WAP's in communication with the first piece of equipment.
5. The wireless locating method of claim 4, wherein determining that the second signal strength profile matches the first signal strength profile includes determining that the signal strengths of the second WiFi messages for a preset number of WAP's of the plurality of WAP's is between the respective minimum signal strength values and maximum signal strength values for each of the preset number of WAP's.

6. The wireless locating method of claim 5, wherein the preset number of WAP's is less than all of the WAP's in communication with the second piece of equipment.

7. The wireless locating method of claim 5, wherein the preset number of WAP's corresponds to a set number of WAP's having highest signal strength from among the plurality of WAP's in communication with the second piece of equipment.

8. The wireless locating method of claim 7, wherein the set number is at least four.

9. The wireless locating method of claim 5, further comprising filtering out anomalous signal strengths of the first WiFi messages from inclusion in the minimum signal strength values and the maximum signal strength values.

10. The wireless locating method of claim 9, wherein the anomalous signal strengths of the first WiFi messages includes signal strengths being below a predetermined signal strength threshold.

11. The wireless locating method of claim 1, further comprising initiating from the locating server a recalibration request to have the equipment ID re-entered manually with the UI of the first piece of equipment if the signal strengths of the first WiFi messages is indicative of one or more obstructions being present at the first location.

12. The wireless locating method of claim 1, further comprising initiating from the locating server a recalibration request to have the equipment ID re-entered manually with the UI of the first piece of equipment if the signal strengths of the first WiFi messages is indicative that a wireless network including the plurality of WAP's has been updated.

13. The wireless locating method of claim 12, wherein the wireless network is determined to be updated by the server in response to one or more WAP's of the plurality of WAP's being removed from the wireless network.

14. The wireless locating system of claim 12, wherein the wireless network is determined to be updated by the server in response to one or more additional WAP's being added to the wireless network.

15. The wireless locating system of claim 1, wherein the second signal strength profile is considered to match the first signal strength profile if one or more of a median, a mean, and a mode value of the signal strength profile of the second messages are between respective minimum and maximum signal strength values of the signal strength profile of the first messages.

16. The wireless locating system of claim 15, wherein determining the signal strengths of the first WiFi messages occurs while the first piece of equipment is situated at the building location, and wherein determining the signals strengths of the second WiFi messages occurs while the second piece of equipment is situated at the building location.

17. The wireless locating system of claim 1, wherein determining the signal strengths of the first WiFi messages occurs while the first piece of equipment is situated at the building location, and wherein determining the signals strengths of the second WiFi messages occurs while the second piece of equipment is situated at the building location.

18. A system for carrying out the method of claim 1, the system comprising one or more of the following: the locating server, the first piece of equipment, the plurality of WAP's, and the second piece of equipment.

19. A nontransitory computer-readable medium having instructions stored thereon for carrying out the method of claim 1.

* * * * *